(12) United States Patent
Oron et al.

(10) Patent No.: US 6,395,016 B1
(45) Date of Patent: May 28, 2002

(54) METHOD OF TREATING A HEART USING CELLS IRRADIATED IN VITRO WITH BIOSTIMULATORY IRRADIATION

(75) Inventors: Uri Oron, Rishon Lezion; Avraham Matcovitch, Nesher, both of (IL)

(73) Assignee: Biosense, Inc., New Brunswick, NJ (US)

( * ) Notice: Subject to any disclaimer, the term of this patent is extended or adjusted under 35 U.S.C. 154(b) by 96 days.

(21) Appl. No.: 09/612,584

(22) Filed: Jul. 7, 2000

Related U.S. Application Data

(63) Continuation of application No. 09/230,399, filed on Nov. 1, 1999.
(60) Provisional application No. 60/034,703, filed on Jan. 3, 1997, and provisional application No. 60/034,704, filed on Jan. 3, 1997.

(30) Foreign Application Priority Data

Jul. 28, 1996 (IL) .................................................. 118968
Jul. 28, 1997 (WO) ................................ PCT/IL97/00257

(51) Int. Cl.[7] .............................................. A61N 5/006
(52) U.S. Cl. ............................. 607/88; 128/898; 607/89
(58) Field of Search ............................... 607/88–92, 50, 607/3; 606/2, 9, 10, 13–17; 424/93; 600/407

(56) References Cited

U.S. PATENT DOCUMENTS

| | | | |
|---|---|---|---|
| 3,900,034 A | 8/1975 | Katz et al. | 128/395 |
| 4,296,100 A | 10/1981 | Franco | 424/108 |
| 4,332,893 A | 6/1982 | Rosenberg | 435/68 |
| 4,353,888 A | 10/1982 | Sefton | 424/25 |
| 4,378,347 A | 3/1983 | Franco | 424/108 |
| 4,503,038 A | 3/1985 | Banda et al. | 424/95 |

(List continued on next page.)

FOREIGN PATENT DOCUMENTS

| | | | |
|---|---|---|---|
| EP | 0 618 225 A1 | 3/1994 | ............ C07K/5/06 |
| EP | 0 710 657 A1 | 8/1996 | ......... C07D/263/24 |
| EP | 0 908 194 A2 | 4/1999 | .......... A61M/25/01 |
| RU | 2022574 C1 | 1/1991 | ............ A61N/2/02 |
| SU | 1715351 A1 | 3/1988 | .......... A61M/39/00 |
| SU | 1806781 A1 | 12/1990 | ............ A61N/2/02 |
| SU | 1792717 A1 | 2/1993 | |
| SU | 2022574 C1 | 11/1994 | |

(List continued on next page.)

OTHER PUBLICATIONS

Fishbein M., Maclean D., Maroko P. (1978) Experimental Myocardial Infarction in the Rat. American Journal of Pathology.90 (1): 57–70.

Grounds M., McGeachie J. (1987) A model of myogenesis in vivo, derived from detailed autoradiographic studies of regenerating skeletal mussele, challenges the concept of quantal mitosis. Cell and Tissue Research.250:563–569.

Felgner P., Gadek T., Holm M., Roman R., Chan H., Wenz M., Northrop J., Ringold G., Danielsen M. (1987) Lipofection: A highly efficient, lipid–mediated DNA–transfection procedure. Proc. Natl. Acad. Sci. USA 84:7413–7417.

(List continued on next page.)

*Primary Examiner*—Michael Peffley
*Assistant Examiner*—Pete Vrettakos
(74) *Attorney, Agent, or Firm*—Louis J. Capezzuto

(57) ABSTRACT

A method of treating a patient's heart comprises the steps of identifying an ischemic area of the heart. A plurality of cells are provided and the cells are irradiated in vitro with electromagnetic radiation. The irradiated cells are then implanted into the ischemic area of the heart. The electromagnetic radiation provides biostimulation of the cells. The treated cells are cardio myocetes such as from embrionic heart muscle or skeletal muscle cells. The electromagnetic radiation is in the infrared (IR) range, visible light range, or ultraviolet (UV) range.

8 Claims, 18 Drawing Sheets

U.S. PATENT DOCUMENTS

| | | | |
|---|---|---|---|
| 4,578,061 A | 3/1986 | Lemelson | 604/164 |
| 4,588,395 A | 5/1986 | Lemelson | 604/59 |
| 4,636,195 A | 1/1987 | Wolinsky | 604/53 |
| 4,668,226 A | 5/1987 | Omata et al. | 604/272 |
| 4,672,963 A | 6/1987 | Barken | |
| 4,686,979 A | 8/1987 | Gruen et al. | 128/303.1 |
| 4,698,301 A | 10/1987 | Weiss et al. | 435/41 |
| 4,699,788 A | 10/1987 | Catsimpoolas et al. | 424/104 |
| 4,709,703 A | 12/1987 | Lazarow et al. | |
| 4,721,672 A | 1/1988 | Vallee et al. | 435/70 |
| 4,769,362 A | 9/1988 | Catsimpoolas et al. | 514/25 |
| 4,778,787 A | 10/1988 | Catsimpoolas et al. | 514/25 |
| 4,788,975 A | 12/1988 | Shturman et al. | 128/303.1 |
| 4,824,436 A | 4/1989 | Wolinsky | 604/53 |
| 4,848,343 A | 7/1989 | Wallsten et al. | |
| 4,871,356 A | 10/1989 | Haindl et al. | 604/247 |
| 4,874,746 A | 10/1989 | Antoniades et al. | 514/21 |
| 4,879,312 A | 11/1989 | Kamarei et al. | 514/560 |
| 4,888,324 A | 12/1989 | Catsimpoolas et al. | 514/25 |
| 4,891,225 A | 1/1990 | Langer et al. | 424/428 |
| 4,895,838 A | 1/1990 | Mccluer et al. | 514/54 |
| 4,900,673 A | 2/1990 | Harper et al. | 435/199 |
| 4,916,073 A | 4/1990 | Vallee et al. | 435/252.3 |
| 4,917,084 A | 4/1990 | Sinofsky | 606/7 |
| 4,921,482 A | 5/1990 | Hammerslag et al. | 604/95 |
| 4,930,504 A | 6/1990 | Diamantopoulos et al. | 128/395 |
| 4,940,730 A | 7/1990 | Wakamatsu et al. | 514/560 |
| 4,950,266 A | 8/1990 | Sinofsky | 606/2 |
| 4,966,597 A | 10/1990 | Cosman | |
| 4,966,847 A | 10/1990 | Stacey et al. | 435/172.3 |
| 5,026,839 A | 6/1991 | Moscatelli et al. | 536/27 |
| 5,035,693 A | 7/1991 | Kratzer et al. | |
| 5,041,109 A | 8/1991 | Abela | |
| 5,053,033 A | 10/1991 | Clarke | |
| 5,073,492 A | 12/1991 | Chen et al. | 435/240.2 |
| 5,078,718 A | 1/1992 | Moll et al. | |
| 5,112,946 A | 5/1992 | Maione | 530/324 |
| 5,125,924 A | 6/1992 | Rudko | 606/12 |
| 5,125,926 A | 6/1992 | Rudko et al. | 606/19 |
| 5,130,141 A | 7/1992 | Law et al. | 424/548 |
| 5,194,596 A | 3/1993 | Tischer et al. | 530/399 |
| 5,195,968 A | 3/1993 | Lundquist et al. | 604/95 |
| 5,219,739 A | 6/1993 | Tischer et al. | 435/69.4 |
| 5,226,430 A | 7/1993 | Spears et al. | |
| 5,244,460 A | 9/1993 | Unger et al. | 604/53 |
| 5,254,112 A | 10/1993 | Sinofsky et al. | |
| 5,275,594 A | 1/1994 | Baker et al. | |
| 5,310,883 A | 5/1994 | Seddon et al. | 530/399 |
| 5,318,957 A | 6/1994 | Cid et al. | 514/8 |
| 5,327,884 A | 7/1994 | Hardy et al. | |
| 5,328,470 A | 7/1994 | Nabel et al. | 604/101 |
| 5,332,671 A | 7/1994 | Ferrara et al. | 435/240.1 |
| 5,346,488 A | 9/1994 | Prince et al. | |
| 5,350,377 A | 9/1994 | Winston et al. | |
| 5,368,564 A | 11/1994 | Savage | 604/95 |
| 5,368,592 A | 11/1994 | Stern et al. | 606/33 |
| 5,370,608 A | 12/1994 | Sahota et al. | 604/20 |
| 5,377,685 A | 1/1995 | Kazi et al. | |
| 5,380,316 A | 1/1995 | Aita et al. | 606/7 |
| 5,383,923 A | 1/1995 | Webster, Jr. | 607/125 |
| 5,385,148 A | 1/1995 | Lesh et al. | 128/662.06 |
| 5,389,096 A | 2/1995 | Aita et al. | 606/15 |
| 5,391,199 A | 2/1995 | Ben-Haim | 607/122 |
| 5,403,356 A | 4/1995 | Hill et al. | 607/14 |
| 5,404,297 A | 4/1995 | Birk et al. | 362/421 |
| 5,409,483 A | 4/1995 | Campbell et al. | |
| 5,417,653 A | 5/1995 | Sahota et al. | 604/20 |
| 5,423,805 A | 6/1995 | Brucker et al. | |
| 5,431,168 A | 7/1995 | Webster, Jr. | 128/658 |
| 5,433,198 A | 7/1995 | Desai | 128/642 |
| 5,445,146 A | 8/1995 | Bellinger | |
| 5,464,436 A | 11/1995 | Smith | |
| 5,465,717 A | 11/1995 | Imran et al. | 128/642 |
| 5,466,596 A | 11/1995 | Breitman et al. | 435/240.2 |
| 5,470,831 A | 11/1995 | Whitman et al. | 514/16 |
| 5,471,982 A | 12/1995 | Edwards et al. | 128/642 |
| 5,480,422 A | 1/1996 | Ben-Haim | 607/122 |
| 5,486,170 A | 1/1996 | Winston et al. | |
| 5,487,391 A | 1/1996 | Panescu | 128/699 |
| 5,554,152 A | 9/1996 | Aita et al. | 606/7 |
| 5,558,073 A | 9/1996 | Pomeranz et al. | 128/642 |
| 5,568,809 A | 10/1996 | Ben-Haim | 128/656 |
| 5,580,859 A | 12/1996 | Felgner et al. | 514/44 |
| 5,587,383 A | 12/1996 | Takatani et al. | 514/300 |
| 5,588,432 A | 12/1996 | Crowley | 128/660.03 |
| 5,602,301 A | 2/1997 | Field | 800/2 |
| 5,607,419 A | 3/1997 | Amplatz et al. | |
| 5,607,918 A | 3/1997 | Eriksson et al. | 514/12 |
| 5,620,438 A | 4/1997 | Amplatz et al. | 606/10 |
| 5,624,433 A | 4/1997 | Radisch, Jr. | |
| 5,641,743 A | 6/1997 | Bohlen et al. | 514/2 |
| 5,641,756 A | 6/1997 | Robinson | 514/44 |
| 5,652,225 A | 7/1997 | Isner | 514/44 |
| 5,661,133 A | 8/1997 | Leiden et al. | 514/44 |
| 5,674,192 A | 10/1997 | Sahatjian et al. | 604/28 |
| 5,693,049 A | 12/1997 | Mersch | 606/15 |
| 5,693,622 A | 12/1997 | Wolff et al. | 514/44 |
| 5,698,531 A | 12/1997 | Nabel et al. | 514/44 |
| 5,707,969 A | 1/1998 | Nabel et al. | 514/44 |
| 5,733,727 A | 3/1998 | Field | 435/6 |
| 5,741,246 A | 4/1998 | Prescott | 606/7 |
| 5,755,752 A | 5/1998 | Segal | 607/89 |
| 5,769,843 A | 6/1998 | Abela et al. | 606/10 |
| 5,776,174 A | 7/1998 | Van Tassel | 607/89 |
| 5,780,052 A | 7/1998 | Khaw et al. | 424/450 |
| 5,785,965 A | 7/1998 | Pratt et al. | 424/93.21 |
| 5,792,453 A | 8/1998 | Hammond et al. | 424/93.21 |
| 5,797,870 A | 8/1998 | March et al. | 604/49 |
| 5,807,384 A | 9/1998 | Mueller | 606/7 |
| 5,807,388 A | 9/1998 | Jeevanandam et al. | 606/15 |
| 5,807,556 A | 9/1998 | Mannion et al. | 424/198.1 |
| 5,810,836 A | 9/1998 | Hussein et al. | 606/108 |
| 5,814,039 A | 9/1998 | Prescott | 606/7 |
| 5,827,203 A | 10/1998 | Nita | 601/2 |
| 5,830,222 A | 11/1998 | Makower | 606/159 |
| 5,830,879 A | 11/1998 | Isner | 514/44 |
| 5,840,059 A | 11/1998 | March et al. | 604/53 |
| 5,840,075 A | 11/1998 | Mueller et al. | 606/7 |
| 5,843,073 A | 12/1998 | Sinofsky | 606/10 |
| 5,843,742 A | 12/1998 | Natsoulis et al. | 435/172.3 |
| 5,846,528 A | 12/1998 | Podsakoff et al. | 424/93.2 |
| 5,858,351 A | 1/1999 | Podsakoff et al. | 424/93.2 |
| 5,865,744 A * | 2/1999 | Lemelson | 600/407 |
| 5,661,133 C1 | 6/1999 | Leiden et al. | 514/44 |
| 5,925,012 A | 7/1999 | Murphy-Chutorian et al. | 604/30 |
| 5,964,757 A | 10/1999 | Ponzi | |
| 6,024,739 A | 2/2000 | Ponzi et al. | |
| 6,027,473 A | 2/2000 | Ponzi | |
| 6,063,108 A * | 5/2000 | Salansky et al. | 607/89 |
| 6,110,459 A * | 8/2000 | Mickle et al. | 424/93.21 |
| 6,151,525 A * | 11/2000 | Soykan et al. | 607/50 |

FOREIGN PATENT DOCUMENTS

| | | | | |
|---|---|---|---|---|
| WO | WO 94/06349 | 3/1994 | | A61B/5/042 |
| WO | WO 94/11506 | 5/1994 | | C12N/15/12 |
| WO | WO 95/01138 | 1/1995 | | A61F/2/06 |
| WO | WO 95/07657 | 3/1995 | | A61B/8/12 |
| WO | WO 95/25807 | 9/1995 | | C12N/15/86 |
| WO | WO 95/29993 | 11/1995 | | C12N/5/10 |
| WO | WO 96/05768 | 2/1996 | | A61B/5/06 |

| WO | WO 96/18303 | 6/1996 | ........... A01N/63/00 |
|---|---|---|---|
| WO | WO 96/26742 | 9/1996 | ........... A61K/48/00 |
| WO | WO 96/39830 | 12/1996 | ........... A01N/43/04 |
| WO | WO 97/11720 | 4/1997 | ........... A61K/48/00 |
| WO | WO 97/14307 | 4/1997 | ........... A01N/43/04 |
| WO | WO 97/23256 | 7/1997 | ........... A61M/29/00 |
| WO | WO 97/24981 | 7/1997 | ......... A61B/5/0215 |
| WO | WO 97/25101 | 7/1997 | ............ A61N/5/00 |
| WO | WO 97/29701 | 8/1997 | ........... A61B/17/22 |
| WO | WO 97/29803 | 8/1997 | ............ A61N/5/06 |
| WO | WO 97/32990 | 9/1997 | ........... C12N/15/86 |
| WO | WO 97/47253 | 12/1997 | ........... A61B/19/00 |
| WO | WO 98/05307 | 2/1998 | ............ A61K/9/22 |
| WO | WO 98/07878 | 2/1998 | ........... C12N/15/86 |
| WO | WO 98/10085 | 3/1998 | ........... C12N/15/86 |
| WO | WO 98/15575 | 4/1998 | ........... C07K/14/47 |
| WO | WO 99/10014 | 3/1999 | ......... A61K/48/00 |
| WO | WO 99/10485 | 3/1999 | ........... C12N/15/10 |
| WO | WO 99/22655 | 5/1999 | ........... A61B/17/32 |
| WO | WO 99/29251 | 6/1999 | ........... A61B/19/00 |
| WO | WO 99/39624 | 8/1999 | ............ A61B/1/31 |

OTHER PUBLICATIONS

Swain J. (1989) Gene Therapy A New Approach to the Treatment of Cardiovascular Tissue. Circulation. 80:1495–1496.

Whalen G., Shing Y., Folkman J. (1989) The Fate of Intravenously Administered bFGF and the Effect of Heparin. Growth Factors. 1:157–164.

Nabel E., Plautz G., Boyce F., Stanley J., Nabel G. (1989) Recombinant Gene Expression in Vivo Within Endothelial Cells of the Arterial Wall. Science. 244:1342–1343.

Pavlath G., Rich K., Webster S., Blau H. (1989) Localization of muscle gene products in nuclear domains. Nature.337:570–573.

Friedmann T. (1989) Progress Toward Human Gene Therapy. Science.244:1275–1281.

Ralston E., Hall Z. (1989) Transfer of a Protein Encoded by a Single Nucleus to Nearby Nuclei in Multinucleated Myotubes. Science.244:1066–1069.

Thomason D., Booth F. (1990) Stable incorporation of a bacterial gene into adult rat skeletal muscle in vivo. American Physiological Society. C578–C581.

Parker T., Packer S., Schneider M. (1990) Peptide Growth Factors Can Provoke "Fetal" Contractile Protein Gene Expression in Rat Cardiac Myocytes. J. Clin. Invest. 85:507–514.

Shubeita H., McDonough P., Harris A., Knowlton K., Glembotski C., Brown J., Chien K. (1990) Endothelin Induction of Inositol Phospholipid Hydrolysis, Sarcomere Assembly, and Cardiac Gene Expression in Ventricular Myocytes. J. of Biological Chemistry. 265(33):20555–20562.

Wolff J., Malone R., Williams Ph, Chong W., Acsadi G., Jani A., Felgner P. (1990) Direct Gene Transfer into Mouse Muscle in Vivo. Science.247:1465–1468.

Nabel e., Plautz G., Nabel G. (1990) Site–Specific Gene Expression in Vivo by Direct Gene Transfer into the Arterial Wall. Science. 249:1285–1288.

Barr E., Leiden J. (1991) Systemic Delivery of Recombinant Proteins by Genetically Modified Myoblasts. Science. 254:1507–1509.

Dhawan J., Pan L., Pavlath G., Travis M., Lanctot A., Blau H. (1991) Systemic Delivery of Human Growth Hormone by Injection of Genetically Engineered Myoblasts. Science. 254: 1509–1512.

Unger E., Banai S., Shou M., Jaklitsch M., Hodge E., Correa R., Jaye M., Epstein S. (1993) A model to assess interventions to improve collateral blood flow: continuous administration of agents into the left coronary artery in dogs. Cardiovascular Research. 27:785–791.

Edelman E., Nugent M., Karnovsky M. (1993) Perivascular and intravenous administration of basic fibroblast growth factor: Vascular and solid organ deposition. Proc. Natl. Acad. Sci. USA. 90:1513–1517.

Abstract: Blau R. (1994) Primary mouse myoblast purification, characterization, and transplantation for cell–mediated gene therapy. J. Cell biol. 125(6):1275–87.

Kazumasa H., Grossman W., Friedman M., Edelman E., Prasad P., Keighley C., Manning W., Sellke F., Simons M. (1994) Basic Fibroblast Growth Factor Improves Myocardial Function in Chronically Ischemic Porcine Hearts. Clinical Invest.94:623–630.

Van Meter C., Claycomb W., Delcarpio J., Smith D., DeGruiter Hl, Smart F., Ochsner J. (1995) Myoblast Transplantation in the Porcine Model: A Potential Technique for Myocardial Repair. The Journal of Thoracic and Cardiovascular Surgery. 110(5): 1442–1448.

Abstract: Chiu R., Zibaitis A., Kao R. (1995) Cellular cardiomyoplasty: myocardial regeneration with satellite cell implantation. Ann. Thorac. Surg. 60(1):12–18.

Abstract: Yoon P., Kao R., Magovern G. (1995) Myocardial regeneration. Transplanting satellite cells into damaged myocardium. Tex. Heart Inst. J. 22(2):119–125/.

Abstract: Taylor D., Atkins B., Hungspreungs P., Jones T., Reedy M., Hutcheson K.,Glower D., Kraus W. (1998) Regenerating functional myocardium: improved perfromance after skeletal myoblast transplantation. Nat. med. 4(8):929–933.

Li R., Mickle D., Weisel R., Mohabeer M., Zhang J., Rao V., Li G., Merante F., Jia Z. (1997) Natural History of Fetal Rat Cardiomyocytes Transplanted into Adult Rat Myocardial Scar Tissue. Circulation. 96(9): 179–187.

Scorsin M, Hagege A., Marotte F., Mirochnik N., Copin H., Barnoux M., Sabri A., Samuel J., Rappaport L., Menasche P. (1997) Does Transplantation of Cardiomyocytes Improve Function of Infarcted Myocardium? Circulation. 96(9): 188–193.

Scorsin M., Marotte F., Sabri A., Le Dref O., Demirag M., Samuel J., Rappaport L., Menasche P. (1996) Can Grafted Cardiomyocytes Colonize Peri–Infarct Myocardial Areas? Circulation. 94(9):337–339.

Leor J., Patterson M., Quinones M., Kedes L., Kloner R. (1996) Transplantation of Fetal Myocardial Tissue into the Infarcted Myocardium of Rat—A Potential Method for Repair of Infarcted Myocardium? Circulation. 94(9):332–336.

Li R., Jia Z., Weisel R., Mickle D., Zhang J., Mohabeer M., Rao V., Ivanov J. (1996) Cardiomyocyte Transplantation Improves Heart Function. Ann. Thorac. Surg. 62:654–661.

Abstract: Murray C., Wiseman R., Schwartz S., Hauschka S. (1996) Skeletal myoblast transplantation for repair of myocardial necrosis. J. Clin. Invest. 11:2512–2523.

Abstract: Lopez J., Simons M. (1996) Local extravascular growth factor delivery in myocardial ischemia. Drug Delivery. 3(3):143–147.

Lopez J., Edelman E., Stamler A., Morgan J., Sellke F., Simons M. (1996) Local Perivascular Administration of Basic Fibroblast Growth Factor: Drug Delivery and Toxicological Evaluation. Drug Metabolism and Disposition. 24(8):922–924.

Simons M., Ware J. (1996) Food for Starving Hearts. Nature Medicine. 2(5):519–520.

Harada K., Friedman M., Lopez J., Wang S., Li J., Pottumarthi P., Pearlman J., Edelman E., Sellke F., Simons M. (1996) Vascular endothelial growth factor administration in chronic myocardial ischemia. The American Physiological Society.1791–1802.

Isner J. (1997) Angiogenesis for revascularization of ischaemic tissues. European Heart Journal. 18:1–2.

Abstract: Irintchev A., Langer M., Zweyer M., Theisen R., Wernig A. (1997) Functional improvement of damaged adult mouse muscle by implantation of primary myoblasts. J. Physiol. 500 (Pt 3): 775–785.

Abstract: Robinson S., Cho P., Levitsky H., Olson J., Hruban R., Acker M., Kessler P. (1996) Arterial delivery of genetically labeled skeletal myoblasts to the murine heart: long–term survival and phenotypic modification of implanted myoblasts. Cell Transplant. 5(1):77–91.

Abstract: Taylor D., Silvestry S., Bishop S., Annex B., Lilly R., Glower D., Kraus W. (1997) Delivery of primary autologous skeletal myoblasts into rabbit heart by coronary infusion: a potential approach to myocardial repair. Proc. Assoc. Am. Physicians. 109(3):245–253.

Ware J., Simons M. (1997) Angiogenesis in ischemic heart tissue. Nature Medicine. 3(2): 158–164.

Taylor D., Atkins B., Hungspreungs P., Jones T., Reedy M., Hutcheson K., Glower D., Kraus W. (1998) Regenerating functional myocardium: Improved performance after skeletal myoblast transplantation. Nature Medicine. 4(8): 929–933.

Abstract: Dorfman J., Duong M., Zibaitis A., Pelletier M., Shum–Tim D., Li C., Chiu R. (1998) Myocardial tissue engineering with autologous myoblast implantation. J. Thorac. Cardiovasc. Surg. 116(5):744–751.

Schwartz Y. (1998) Therapeutic Angiogenesis Overview.

Vale P., Losordo D., Tkebuchava T., chen D., Milliken C., Isner J. (1999) Catheter–Based Myocardial Gene Transfer Utilizing Nonfluoroscopic Electromechanical Left Ventricular Mapping. Journal of the American College of Cardiology. 34(1):246–254.

Licking E. (1999) Gene Therapy—One Family's Story. Business Week. Jul.: 94–104.

Yaakobi T., Maltz L., Oron U. (1996) Promotion of Bone Repair in the Cortical Bone of the Tibia in Rats by Low Energy Laser (He–Ne) Irradiation. Calcified Tissue International. 59:297–300.

Bibikova A., Weiss N., Oron U. (1992) Enhancement of skeletal muscle regeneration following injury in the toad and rat by He–Ne and Ga–As–diode laser irradiation. Monduzzi Editore S.p.A.—Bologna (Italy). 87–90.

Bibikova A., Oron U., (1994) Attenuation of the Process of Muscle Regeneration in the Toad Gastrocnemius Muscle by Low Energy Laser Irradiation. Lasers in Surgery and Medicine. 14:355–361.

Bibikova A., Oron U. (1993) Promotion of Muscle Regeneration in the Toad (*Bufo viridis*) Gastrocnemius Muscle by Low–Energy Laser Irradiation. The Anatomical Record. 235:374–380

Weiss N., Oron U. (1992) Enhancement of muscle regeneration in the rat gastrocnemius muscle by low energy laser irradiation. Anatomy and Embryology. 186:497–503.

Barushka O., Yaakobi T., Oron U. (1995) Effect of Low–Energy Laser (He–Ne) Irradiation on the Process of Bone Repair in the Rat Tibia. Elsevier Science Inc. vol. 16 No. 1: 47–55.

Bibikova A., Belkin V., Oron U. (1994) Enhancement of angiogenesis in regenerating gastrocnemius muscle of the toad (*Bufo viridis*) by low–energy laser irradiation. Anatomy and Embryology. 190:597–602.

Bibikova A., Oron U. (1995) Regeneration in Denervated toad (*Bufo viridis*) Gastrocnemius Muscle and the Promotion of the Process by Low Energy Laser Irradiation. The Anatomical Record. 241:123–128.

Lee G., Ikeda R., Theis J., Stobbe D., Ogata C., Liu H., Reis R., Mason D. (1983) Effects of laser irradiation delivered by flexible fiberoptic system on the left ventricular internal myocardium. American Heart Journal. vol. 106. No. 3:587–590.

Mirhoseini M., Shelgikar S., Cayton M. (1993) Transmyocardial Laser Revascularization: A Review. Journal of Clinical Laser Medicine & Surgery. vol. 11, No. 1: 15–19.

Bonn D. (1996) High–power lasers help the ischaemic heart. The Lancet. vol. 348:118.

P.P. Rumynastev, "Growth and hyperplasia of cardiac muscle cells", B.M.Carlson ed., Harwood New York, 1991, pp. 3–68.

M.C. Fishbein et al., "Experimental myocardial infarction in the rat", Am. J. Pathol 90, 1978, pp. 57–70.

W. Ganz et al., "Intracoronary thrombolysis involving myocardial infarction", Am. Heart 101, 1983, pp. 4–13.

A.R. Gruentzig et al., "Long–term follow–up after percutaneous transluminal coronary angioplasty", N. England J. Med. 316, 1987, pp. 1127–1132.

G.M.Fitzgibbon et al., Coronary bypass graft fate: long term angiographic study, J. Am. Coll. Cardiol. vol. 17 No. 5, 1991, pp. 1075–1080.

M. Belkin et al., "A critical review of low energy laser bioeffects"; Lasers and Light in Ophthalmol. vol. 2 No. 1, 1988, pp. 63–71.

T. Karu, "Photobiology of low–power laser effects", Health Phys. vol. 56 No. 5, 1989, pp. 691–704.

N. Kipshidze et al., "Intravascular laser therapy of acute myocardial infarction", Angiology, Sep. 1990, pp. 801–808.

A.R. Mester, "Modalities of low power laser applications", Galletti et al. (eds.) in "Laser applications in medicine and surgery", Monduzzi Editore, 1992, pp. 33–40.

V.I. Ruzov and K.S. Baltrushaitis, "Ultrastructural changes in the myocardium under the action of the helium–neon laser and obzidan", Vopr. Kurotol. Fizioter. Lech. Fiz. Kult. 5–6, 1992, pp. 62–64.

V.I. Ruzov and K.S. Baltrushaitis, "The microcirculator bed of the ischemic myocardium under the combined action of a low–intensity helium–neon laser and finoptin", Vopr. Kurotol. Fizioter. Lech. Fiz. Kult. 4, 1993, pp. 31–33.

V.I. Ruzov and L.A. Rishkus, The effect of the helium–neon laser on the cyclic nucleotide level in experimental hypodynamia, Vopr. Kurotol. Fizioter. Lech. Fiz. Kult. 2, 1992, pp. 51–53.

V.I. Ruzov, "A comparative study of the action of the helium–neon laser, perlinganite and heparin on the energy apparatus of the ischemic myocardium", Vopr. Kurotol. Fizioter. Lech. Fiz. Kult. 1, 1994, pp. 33–35.

\* cited by examiner

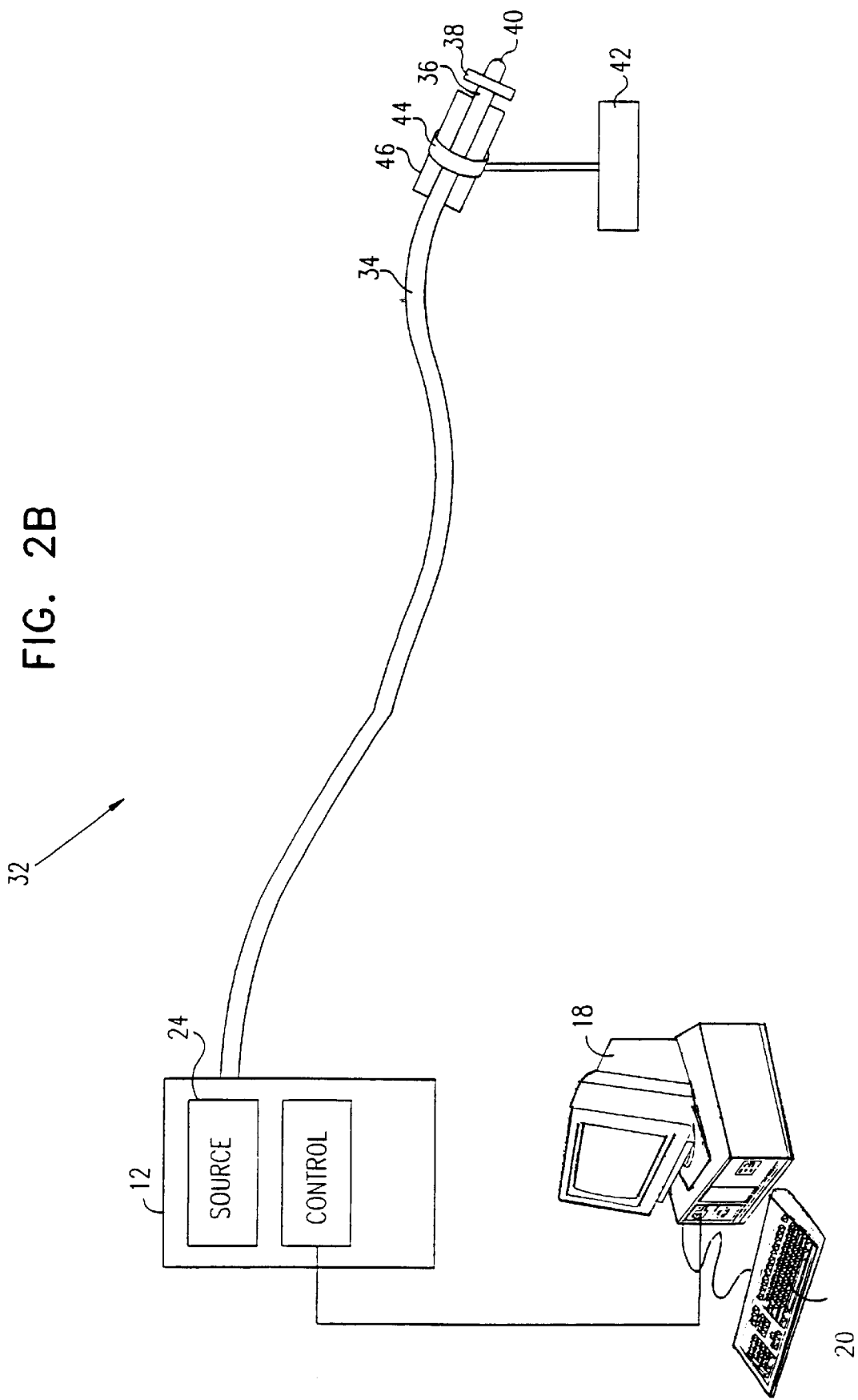

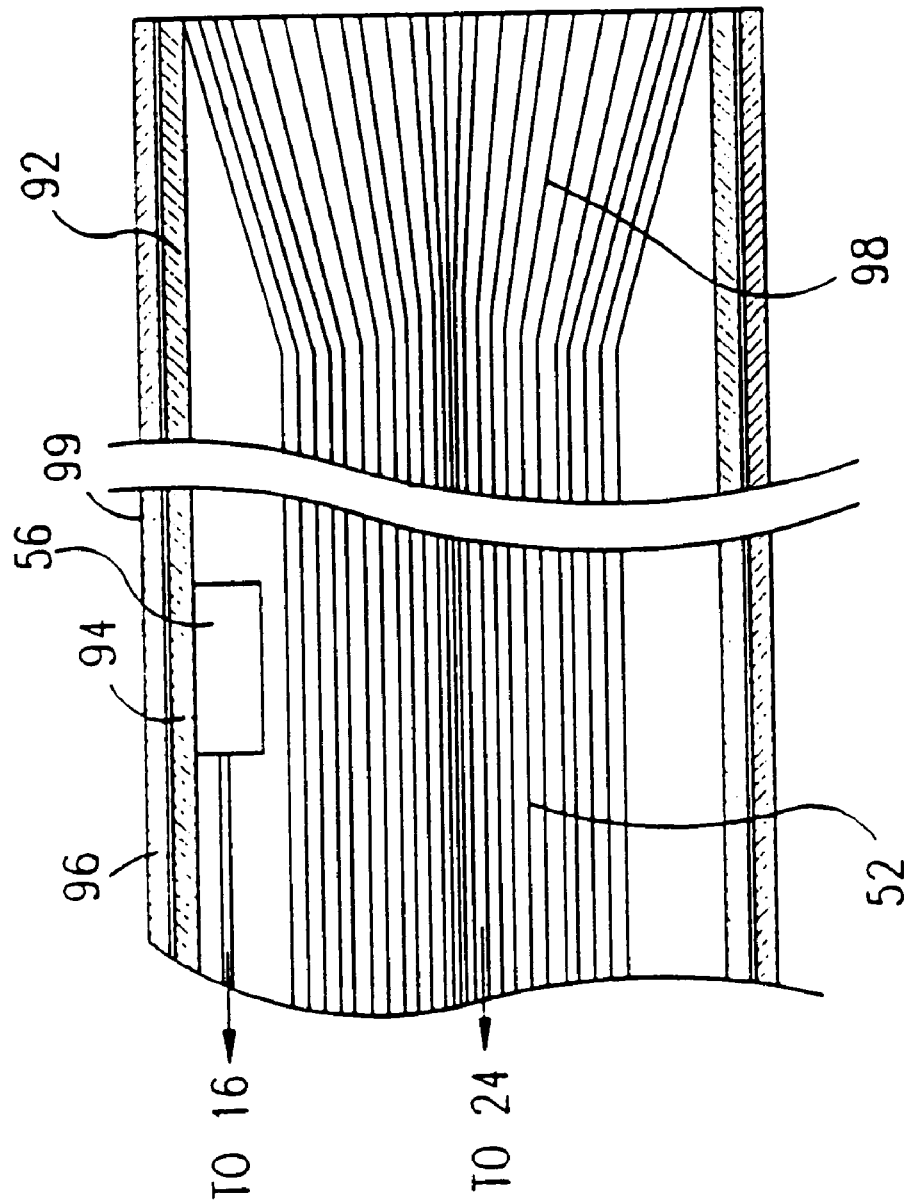

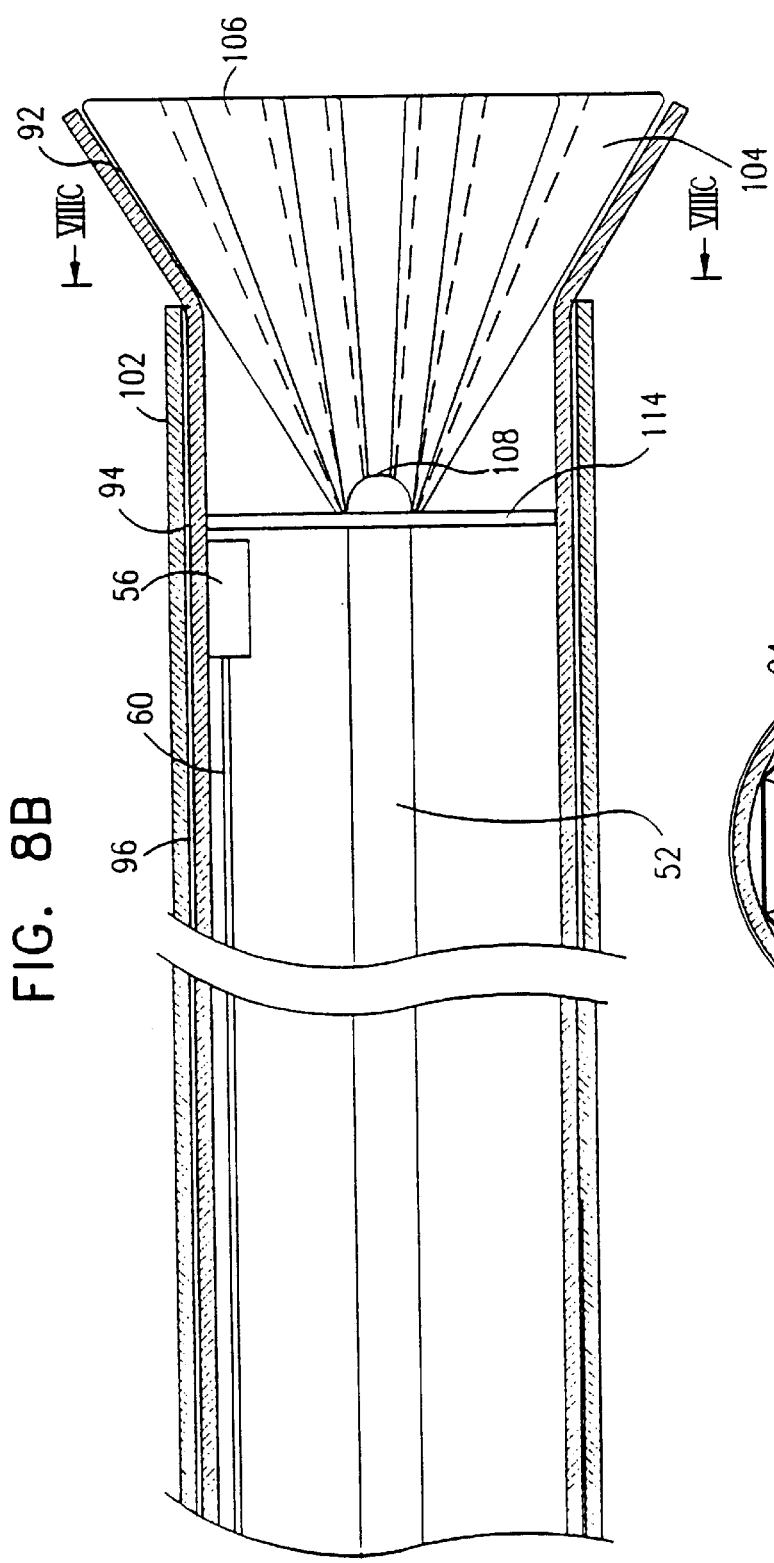
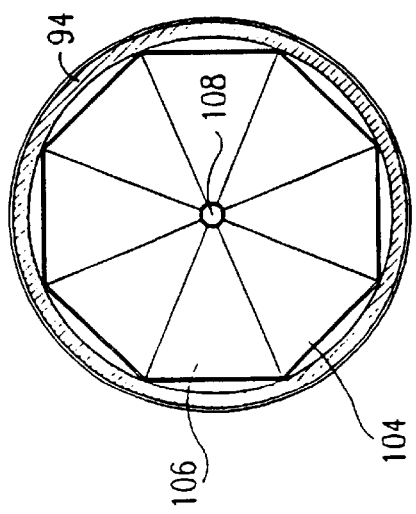

METHOD OF TREATING A HEART USING CELLS IRRADIATED IN VITRO WITH BIOSTIMULATORY IRRADIATION

RELATED APPLICATIONS

This patent application is a continuation of application Ser. No. 09/230,399 filed Nov. 1, 1999 and claims priority from Israel Patent Application 118,968 filed Jul. 28, 1996, and from PCT Patent Application PCT/IL97/00011, filed Jan. 14, 1997, both of which are assigned to the assignee of the present patent application. This patent application also claims the benefit of U.S. Provisional Patent Application Nos. 60/034,703 and 60/034,704, both filed Jan. 3, 1997, which are assigned to the assignee of the present patent application. All of these related applications are incorporated herein by reference.

FIELD OF THE INVENTION

The present invention relates to methods and apparatus for cardiac treatment generally, and particularly to methods and apparatus for improvement of heart function following myocardial infarction and other ischemic heart conditions.

BACKGROUND OF THE INVENTION

Heart disease or heart failure following myocardial infarction is still the major cause of death in the western world. The mature heart muscle (myocardium) cells of mammals are those that reach their last stage of differentiation and, therefore, are considered unable to undergo proliferation (see P. P. Rumynastev, Growth and Hyperplasia of Cardiac Muscle Cells, B. M. Carlson, ed., Harwood, New York, 1991, pp. 3–68). Thus, the myocardium may be afflicted with hypertrophy (increase in cell mass and not cell number) due to mechanical stress or ischemia (inadequate oxygen supply to the cells). Following ischemia, due to occlusion of blood supply to the cells during myocardial infarction (MI), irreversible, physiological changes occur in the cells, which degenerate and are replaced by non-contracting scar tissue (infarcted zone) with time (see M. C. Fishbein, M. B. McLean et al., Experimental myocardial infarction in the rat, Am. J. Pathol. 90: 57–70, 1978).

In particular, cells of the myocardium traumatized by ischemia enter a toxic ischemic cascade resulting in a number of damaging processes to the cells, such as membrane breakdown, mitochondrial disruption, enhanced proteolysis, etc., mainly as the result of unbalanced rates of energy production and consumption. Under conditions of poor oxygen availability, an anaerobic glycolytic pathway replaces the aerobic metabolism as the primary source of adenosine triphosphate (ATP), facilitating cell survival. The anaerobic glycolytic metabolism and related anaerobic cell survival, however, is a short-lived mechanism, as this natural up-regulation of glycosis is stopped by the accumulation of lactate, which inhibits the key glycolytic enzyme phosphofructokinase (PFK) (see E. Hofiann, The significance of phosphofructokinase to the regulation of carbohydrate metabolism, Rev. Physiol. Biochem. Pharmacol. 75: 2–68, 1976).

Current clinical treatments of acute MI include thrombolytic treatment (W. Ganz, N. Buchbinder, H. Marcus et al., Intracoronary thrombolysis involving myocardial infarction, Am. Heart 101: 4–10, 1983); PTCA (coronary angioplasty) performed on occluded arteries (A. R Gruentzig et al., Long-term follow-up after percutaneous transmural coronary angioplasty, N. Engl. J. Med. 316: 1127–32, 1987); and also bypass surgery as near as possible to the occurrence of the MI (G. M. Fitzgibon, A. J. Leach, H. P. Kafka et al, Coronary bypass graft fate: long-term angiographic study, J. Am. Coll. Cardiol. 17: 1075–80, 1991). These procedures are expensive, demand very highly qualified personnel and physicians, and are not always practically possible in health care. Moreover, these methods endeavor to alter the consequences of the irreversible ischemic injury that occurs in the cells rather than inhibit such consequences. It should be mentioned that even with qualified personnel and first-rate treatment, the above procedures are not always successful.

Several attempts have been made in the past to reduce the infarcted area in the myocardium following induction of MI in experimental animals. These include the use of corticosteroids, various antioxidant agents, and chemical agents for prolonging anaerobic cell survival.

Exogenous fructose-1,6-diphosphate (FDP) was found to bypass the PFK block and restore anaerobic ATP and creatine phosphate (CP) production (see A. K. Markov, N. C. Oglethorpe, et al., Hemodynamic electrocardiographic and metabolic effects of fructose diphosphate on acute myocardial ischemia, Am. Heart J. 100: 639–646, 1980). In experiments performed on animals, FDP was found to improve hemodynamic parameters, reduce arrhythmias and infarct size, and increase survival rate. (See A. K. Markov, N. C. Oglethorpe, et al., op. cit., and J. W. Starnes, K. S. Seiler, et al., Fructose-1,6-diphosphate improves efficiency of work in isolated perfused rat heart, Am. J. Physiol. 262: M380–M384, 1992. All of these articles are incorporated herein by reference.)

Ischemic cardiac tissues may have their blood supply restored, using various treatments known in the art, such as coronary angioplasty. In the course of such a treatment, the ischemic tissue may be rapidly reperfused with blood. Such rapid reperfusion has been shown, at least in some cases, to result in post-reperfusion injury, i.e., damage induced by the reperfusion per se. The injury may be caused, inter alia, by superoxides formed within the tissue due to a sharp increase in oxygen supply following the reperfusion procedure. Superoxides are highly-reactive, toxic free radical substances, which undergo detrimental, undesirable reactions with organic and inorganic cellular substances. Indigenous and/or exogenous antioxidants alleviate the toxic effect of the superoxides by either preventing their formation or scavenging the free radicals immediately upon formation. Use of exogenous free radicals scavengers for alleviation of post-reperfusion injury in heart muscle has recently been reported (see E. P. Chen et al., Extracellular superoxide dismutase transgene overexpression preserves post-ischemic myocardial function in isolated murine hearts, Circulation, 94:412–417, 1996, which is incorporated herein by reference). In particular, non-toxic seleno-organic free radical scavengers were found to exhibit such a cytoprotective effect (see V. Ullrich, et al., Seleno-binding equilibria between plasma and target proteins, Biochem. Pharmacol. 52:15, 1996, which is incorporated herein by reference).

Implantation of cells from skeletal muscle origin or of embryonic heart muscle cells (cardiomyocytes) into ischemic or infarcted regions of the heart has recently been reported (see R. K. Li et al., Cardiomyocyte transplantation improves heart function, Ann. Thorac. Surg. 62:454–460, 1996, which is incorporated herein by reference). The implanted cells survived the implantation and remained viable for a period of at least several weeks thereafter. The cells, implanted into a cold injury site of the left ventricle myocardium of rats, were reported to significantly improve the heart function (with respect to various physiological parameters) in comparison with control rats, which had not undergone cells implantation. In experiments on mice performed (see J. E. Morgan et al., Yield of normal muscle from precursor cells implanted into preirradiated and nonirradiated legs of young and old max mice, Muscle & Nerve 19:132–139, 1996, which is incorporated herein by reference), only about 10% of the implanted cells of skeletal muscle origin survived the implantation and remained viable for a period of few weeks after the implantation.

Low power laser irradiation has recently been found to modulate various processes in different biological systems (see M. Belkin, B. Zaturunsky, and M. Schwartz, A critical review of low power laser bioeffects, Laser Light Ophthalmol. 2: 63–71, 1988, and T. Karu, Photobiology of low power laser effects, Health Phys. 56: 691–704, 1988). For example, in isolated mitochondria, He—Ne laser irradiation (5 J/cm$^2$) elevated membrane potential and production of ATP, while in isolated fibroblasts with the same radiation, an increase in collagen production was observed. The effect of low power laser irradiation on regeneration processes following trauma has thus far been investigated in the skin, the peripheral nervous systems, skeletal muscles and bone. It has been found that laser irradiation given at the right time and energy level modulates the process of skeletal muscle regeneration and, in most systems, causes a faster recovery after trauma and an enhanced rate of regeneration in muscles and bone (see N. Weiss and U. Oron, Enhancement of muscle regeneration in the rat gastrocnemius muscle by low power laser irradiation, Anat. Embryol. 186: 497–503, 1992, and O. Barushka, T. Yaakobi and U. Oron, Effect of laser irradiation on the process of bone repair in the rat tibia, Bone 16: 47–55, 1995). Low power laser irradiation has also been found to induce a twofold increase in new blood vessels formation (i.e., angiogenesis) in the injured zone of skeletal muscles (see A. Bibikova, N. Belkin and U. Oron, Enhancement of angiogenesis in regenerating gastrocnemius muscle of the toad by low energy laser irradiation, Anat. Embryol. 190:597–602, 1994, which is incorporated herein by reference).

In a recent study, the effect of irradiation of the blood (subclavian artery) by He—Ne lasers in patients after MI was observed (see N. N. Kipshidze et al., Intravascular laser therapy of acute myocardial infarction, Angiology 801–808, September 1990, which is incorporated herein by reference). The study reports a better recovery of the laser-irradiated patients in terms of the levels of enzyme activity (creatine phosphokinase) in blood (which was lower in the irradiated patients) and a reduction of arrhythmia of the heart.

It is to be emphasized that the Kipshidze et al. paper does not teach biostimulation of the myocardium itself but rather of the blood. The authors write in the Abstract "A new method for . . . using monochromatic He—Ne laser . . . this paper deals with the effect of endovascular (inside blood vessels) laser blood irradiation on high-grade arrhythmias". On page 802, lines 2–3, it states that "Endovascular laser therapy was performed using an LG-75 laser via an optical light guide introduced into the lumen of the superior vena cava . . .". Thus, the myocardium was not irradiated but rather the blood.

It is known in the art (see Mester, A. R., Modalities of low power laser applications, Galletti et al. (eds.) *Laser Applications in Medicine and Surgery*, Monduzzi Editore (1992), pp. 33–40) that the energy emitted from a He—Ne laser, even with high power, is absorbed by hemoglobin in the red blood cells and by living tissues. This type of energy at the specific wavelength (632.2 nm) does not penetrate well through living tissues. The loss in power output is about 90% after 2 mm depth of tissue and there is practically no power capable of penetrating beyond 3 mm depth of tissue with a moderate blood supply. It is also acknowledged in the art that exposure of the tissue to power less than 4 mW has no biostimulatory effect on tissues (see Galletti et al. ibid. and Bradley, P. F. and B. Gursoy, Penetration studies of low intensity laser therapy (LILT) wavelength, Proc. WALT 1996, p. 18.).

Thus, when energy from the He—Ne laser source (the power level is not cited in the Kipshidze et al. work, but can be at most 40 mW) is conveyed through an optical fiber (which causes a loss of approximately 30–40% of the source), it ends up at the tip of an optical fiber at no more than 25 mW. Since the tip is situated in a blood vessel (superior vena cava) which is at least 5 cm in distance from the heart muscle, the energy which is absorbed by the heart muscle from the optical fiber is practically zero and has no biostimulatory effect on the heart muscle based on the above scientific knowledge.

Other studies have reported qualitative alternations in the ultrastructure of musculature (see Ruzov, I. V. and Baltrushaitis, K. S., Ultrastructural changes in the myocardium under the action of the helium-neon laser and obzidan, Vopr. Kurotol. Fizioter. Lech. Fiz. Kult. 5–6: 62–4, 1992), blood vessels (see Ruzov, I. V. and Baltrushaitis, K. S., The microcirculatory bed of the ischemic myocardium under the combined action of a low-intensity helium-neon laser and finoptin, Vopr. Kurotol. Fizioter. Lech. Fiz. Kult. 4: 31–3, 1993) and mitochondria of the myocardium of rabbits in a hypodynamic stage following irradiation of the blood by He—Ne laser (see Ruzov, I. V. and Rishkus, L. A., The effect of the helium-neon laser on the cyclic nucleotide level in experimental hypodynamia, Vopr. Kurotol. Fizioter. Lech. Fiz. Kult. 2:51–53, 1992). The irradiation in the above studies was performed by insertion of fiber optics through the ear vein in the ear of the rabbits. It should be emphasized that in the Russian Republic, irradiation of blood by UV or low power lasers is a common procedure towards a better recovery in many human illnesses (see Ruzov, I. V. A comparative study of the action of the helium-neon laser, perlinganite and heparin on the energy apparatus of the ischemic myocardium. Vopr. Lech. Fizioter. Lech. Fiz. Kult. 5–6: 62–4, 1994).

In the four aforementioned scientific papers by Ruzov et al, the authors use an experimental system of He—Ne laser at a power level of 1.5 mW, similar to Kipshidze et al. Again, the energy was introduced by fiberoptics into a vein in the ear of a rabbit. As mentioned above with reference to the paper by Kipshidze et al., the energy that is finally transmitted from the vein in the ear to the heart muscle is practically zero, without any expected biostimulatory effects on ischemic or hypodynamic heart muscle, as mentioned in these scientific papers.

Russian Patent 1715351 to Golikov et al., relates to irradiation treatment by a He—Ne laser at acupuncture points to help recovery of heart disease in the post-infarction period. However, this patent can not relate to irradiation of the myocardium because the He—Ne laser beam, even if aimed at points on the chest of a human patient above the heart, cannot penetrate more than 2–3 mm. Thus, practically no laser energy can reach the heart muscle since the muscle between the ribs in humans is at least 3 cm thick. The positive effects achieved in laser irradiated patients, is perhaps due to acupuncture treatment or reflexogenic therapy, as cited by the authors themselves in the last paragraph of the patent.

Russian patent 1806781 to Leveshunov et al., deals with magnetic-laser treatment to improve clinical prognosis of patients with complicated acute myocardial infarction. Pulsed laser irradiation and infrared radiation (wavelength not mentioned) are applied to the patients' chest wall. There is no known data in the art on the bioeffects of combination of magnetic field and laser irradiation on tissues. The pulsed laser, as suggested in this patent, has a mean power of 12 mW, while the continuous infrared radiation has a power of 50 mW. However, the laser beam has to penetrate through the chest skin and muscles between the ribs with a total average tissue width of about 3 to 5 cm before reaching the heart muscle. Since the laser power diminishes within living tissue in an exponential manner with respect to depth, the maximal laser power output incident on the heart, as suggested by Leveshunov et al., will be reduced through the thick chest wall of a patient to a practically zero, obviously too low to cause any stimulatory effect on the heart muscle.

SUMMARY OF THE INVENTION

The present invention seeks to provide methods and apparatus for improvement of heart function, reduction of scar tissue formation and/or enhancement of the regeneration of myocardial tissue following myocardial infarction, or other heart failure syndromes, by electromagnetic radiation.

Methods in accordance with preferred embodiments of the present invention are based on stimulating myocardial tissue of a patient by irradiation of the tissue with electromagnetic radiation. In the context of the present patent application and in the claims, such methods are referred to as electromagnetic cardiac biostimulation (ECB). ECB in accordance with the principles of the present invention is not limited to any particular range of wavelengths, but the best mode of carrying out the invention is believed to be based on irradiation in the range including infrared (IR), visible light and ultraviolet (UV) radiation. The choice of which particular wavelength, power level, duration of irradiation and number of irradiation sessions is made in accordance with the patient's needs.

Preferably, the radiation used in ECB is coherent, such as radiation provided by a laser, but it may alternatively be non-coherent, such as provided by a xenon lamp.

Possible therapeutic effects of biostimulation of infarcted myocardium include a reduction in the size of an infarct, regeneration of cardiomyocytes in the infarct, preservation of the structure and activity of mitochondria in cardiomyocytes, and improved function of diseased myocardium. It is a particular feature of some aspects of the present invention to use electromagnetic radiation to cause regeneration and cytoprotection of cardiomyocytes, following acute ischemia, including preserving the structure and orientation of contractile proteins in the cardiomyocytes, since heretofore, there has been no method known in the art for regeneration and cytoprotection of cardiac muscle under these circumstances. In some preferred embodiments of the present invention, the method of ECB is non-invasive both to the body and to the heart, such as by placing a radiation source against the skin of the patient and irradiating the myocardium therefrom. In other preferred embodiments, some body tissue, such as non-myocardial muscle tissue in the chest or the back of the patient, may be at least partially exposed surgically, and the heart is irradiated therefrom. Although this option is partially invasive to the body, it has the advantage of allowing the radiation to penetrate through a thinner muscle layer, so as to attain a higher, more optimal radiative power on the heart muscle. In still other preferred embodiments, the ECB method may be invasive to the heart, such as by irradiating the heart by means of a catheter introduced into a coronary artery or through a blood vessel into a chamber of the heart.

In some preferred embodiments of the present invention, an ECB method includes a combination of biostimulation by electromagnetic radiation and additional post-infarct clinical treatments, to achieve synergetic effects. Such treatments may include administration of chemical compounds and drugs, such as FDP or non-toxic seleno-organic free radical scavengers, as described above, and laser myocardial revascularization (LMR) procedures, as are known in the art.

LMR is a technique known in the art for creating channels in ischemic heart tissue to improve the blood supply thereto. PCT patent application no. PCT/IL97/00011, filed Jan. 14, 1997, which is assigned to the assignee of the present patent application and incorporated herein by reference, describes LMR in detail. In some preferred embodiments of the present invention, methods and apparatus of LMR described in the PCT/IL97/00011 application are preferably used in conjunction with ECB to effect synergetic healing of ischemic zones of the heart, as described below. The ECB irradiation is preferably performed during a LMR procedure, so as to irradiate the ischemic area and the channels generated therein. The irradiation enhances healing of the channels and ischemic area and stimulates angiogenesis in the vicinity of the LMR channels, as mentioned above (see A. Bibikova et al., 1994).

As descibed above, FDP is believed to partially inhibit (post-infarct) ischemia by re-activating anaerobic glycolysis. It may also alleviate post-reperfusion injury by accelerating the replenishment of high energy metabolites such as ATP and CP. Non-toxic seleno-organic free radical scavengers are also believed to exhibit cytoprotective effects, by inhibiting the toxic effects of reperfusion-generated superoxides, thus alleviating post-reperfusion injury, as mentioned above. Similarly, in accordance with principles of the present invention, low-power laser irradiation of the infarcted zone immediately after acute MI is believed to protect the energy-producing organelles in the cells (mitochondria) from acute damage. Administration of FDP or non-toxic seleno-organic free radical scavengers, which act as cytoprotective agents when delivered to the infarcted area through the blood system, in conjunction with local treatment by ECB, is expected to synergistically intensify healing effects on infarcted myocardial zones. Therefore, in accordance with another preferred embodiment of the present invention, ECB irradiation is performed, preferably closely following the occurrence of an infarct, in conjunction with intravenous administration of exogenous FDP or non-toxic seleno-organic free radical scavengers. The combined effect of the irradiation and the drugs preserves structure and activity of mitochondria in a more effective way.

In some preferred embodiments of the present invention, an ECB device comprises at least one electromagnetic radiation source; relay optics, preferably comprising at least one waveguide, which is coupled to the at least one electromagnetic radiation source; and a lens, for directing radiation from the waveguide onto heart tissue. Preferably, the ECB device further comprises a position sensor, which facilitates the positioning of the waveguide and lens, and a control unit which controls the various functions of the ECB device, including modulation of the source output power and spectrum, duration of the irradiation and positioning. Preferably, the ECB device comprises a visible light source and a light guide optically coupled thereto, preferably a fiberoptic light guide, for the observation of the irradiating during some ECB procedures.

In accordance with a preferred embodiment of the present invention, the at least one electromagnetic radiation source comprises a source of coherent light. The source of coherent light may include a diode laser. Preferably, the diode laser has a power output in the range of 5 mW to 5 W and a wavelength in the range of 250 to 940 nm.

Alternatively, electromagnetic radiation source comprises a source of non-coherent light, preferably, a high intensity xenon lamp. Preferably, the xenon lamp has a power flux of 30 to 500 mW/cm$^2$.

In preferred embodiments of the present invention, the relay optics and position sensor are contained within a catheter for introduction into a chamber of the heart or into a coronary artery for intracardiac irradiation. Most preferably, the catheter is disposable and comprises at least one waveguide, a lens, and a position sensor, for example a magnetic position sensor, as described in PCT patent publication number WO96/05768, which is incorporated herein by reference, to enable navigation and location of the catheter following a viability map, as described below.

In further preferred embodiments of the present invention, the catheter comprises a sensor for determining viability or non-viability of the myocardial tissue. Such sensors may comprise one or more electro- or mechano-physiological detectors, which sense local myocardial electrical or mechanical activity, respectively, as described, for example, in U.S. patent application Ser. No. 08/595,365, which is assigned to the assignee of the present patent application, and in U.S. Pat. No. 5,568,809, both of which are incorporated herein by reference. The viability data gathered in conjunction with location coordinates is used to generate a viability map on which the ischemic regions to be irradiated are identified.

Alternatively or additionally, such sensors may also be used post-irradiation to assess irradiation efficacy in promoting preservation of the heart muscle following ischemic damage. Optionally, the detectors may be used in between ECB sessions to assess efficacy and/or to update the viability map.

Blood and muscular tissue have very high extinction coefficients with respect to biostimulatory electromagnetic radiation wavelengths. Hence, biostimulatory radiation has to be applied in close proximity to, and preferably in contact with, the target area. Accordingly, in some preferred embodiments of the present invention, the catheter comprises one or more proximity or contact sensors, known in the art, for sensing and assuring contact between the catheter and the wall of the heart chamber.

In alternative preferred embodiments of the present invention, mainly those employing non-invasive ECB methods, the ECB apparatus is used in conjunction with an echo ultrasound transducer which communicates with an echo imaging device. The echo transducer provides positional information regarding the infarct and facilitates aiming the irradiating optics to the infarcted heart zones during irradiation. Most preferably, the echo transducer is fastened to the electromagnetic radiation optics, so as to substantially maintain them in a fixed spatial relationship with each other.

In some preferred embodiments of the present invention, the ECB apparatus is adapted to operate in conjunction with LMR procedures, for example those described in PCT application IL97/00011, mentioned above. Accordingly, an integrated catheter, which is adapted for the combined operation, comprises at least one waveguide coupled to the LMR laser source, at least one waveguide coupled to the ECB electromagnetic radiation source, suitable optics, at least one position sensor and, optionally, at least one physiological detector, such as an electrode, for sensing physiological activity in the heart muscle.

Typically, ischemic zones in the myocardium may comprise up to 10 cm$^2$ in area, whereas the typical cross section of an intracardiac catheter is several mm$^2$. Moreover, as noted above, biostimulatory wavelengths do not penetrate substantially more than a few millimeters through blood or muscular tissue. The steep decay of power level restricts the maximal distance between the radiation emitting area and the target area and/or the minimal allowable electromagnetic radiation source power output. Employing a small radiation emitting area for the irradiation of a significantly larger target makes the procedure tedious and time-consuming.

Accordingly, it is an object of some aspects of the present invention to provide radiation-conveying catheters, which spread the radiation over an extended target area, preferably an area larger than a cross-section of the catheter itself, while still enabling efficient energy transfer from the catheter to the tissue. In some preferred embodiments of the present invention, an ECB catheter, for invasive irradiation of the heart, comprises a wide angle lens, for example, a fish-eye lens, as is known in the art, to widen the irradiation beam, at the distal end of the catheter. Alternatively, the widening of the radiation emitting area is achieved by employing a side-emitting or widening optical tip catheter, as described below. Preferably, the optics in the catheter are designed to provide a generally uniform level of irradiation over as substantial portion of the target area.

In some preferred embodiments of the present invention, a side-emitting ECB catheter comprises a longitudinally-disposed radiation-emitting element, for example, a window or lens, for delivering radiation in a radial direction over a substantial portion of the length of the catheter adjacent a distal end thereof. The radiation-emitting element is coupled to the waveguide, which transmits the radiation from the electromagnetic radiation source, and is preferably fitted in a slot or cutaway section along the distal portion of the catheter. Most preferably, the radiation-emitting element is 2 to 3 cm long and 0.2 to 0.3 cm wide, forming a radiation emitting area of approximately 0.5 cm$^2$. Optionally, it has a curved outer surface, which further increases the effective area of irradiation of the element.

As mentioned above, the radiation-emitting element is preferably brought into close proximity to or contact with the target area. Accordingly, in some of these preferred embodiments, the distal portion of the side-emitting catheter is designed to conform to the inner surface of the heart wall when pressed thereagainst, as described in U.S. Provisional Patent Application 60/034,704, which is assigned to the assignee of the present application and incorporated herein by reference. Preferably, as described in the 60/034,704 application, the catheter includes one or more position sensors and/or pressure or proximity sensors, which are used to ascertain the position and orientation of the radiation-emitting element against the heart wall during irradiation.

Alternatively, the catheter may comprise a slanted tip, including a generally elliptical radiation-emitting area, angled with respect to the catheter's longitudinal axis. Preferably, the elliptical area has an outwardly curved surface, for further increasing the effective irradiation area, as described above.

In alternative preferred embodiments of the present invention, the catheter comprises a widening optical tip, which is maintained in a narrow configuration during insertion into the body, but then stretches open after insertion, so as to considerably increase the tip area that is brought into contact with and irradiates the heart tissue. Such a tip may comprise, for example, a fiberoptic bundle, or a radiation-reflecting surface, such as foldable parabolic or multifaceted reflector, surrounding a point-like radiation source, such as the distal tip of the waveguide. Optionally, the widening tip may comprise an optical membrane, as for example a scattering membrane, a layered polarizer membrane, translucent membrane or any other suitable optical membrane known in the art, to spread and/or diffuse the radiation emitted by the waveguide.

In some alternative preferred embodiments of the present invention, the catheter comprises a radiometric sensor, which is placed in or against myocardial tissue to be irradiated so as to measure the local instant radiation power level incident on the tissue and the total irradiative energy supplied to the tissue during an ECB session. The power and the energy level readings may be employed for modulation of the ECB source output power level and for determination of a session's duration. Optionally, the readings may serve to ascertain successful transmission of the ECB radiation from the source through the relay optics and to the designated heart tissue area.

Intravascular irradiation of the blood using a 5 to 50 mW He—Ne laser has been shown to improve heart function (see N. N. Kipshidze, mentioned above). It is believed by the inventors of the present patent application that the He—Ne laser irradiation may also have a beneficial effect on the atherosclerotic process in coronary arteries, and the combination of such irradiation with biostimulatory irradiation of ischemic zones may prove synergistically beneficial to the heart function following acute myocardial infarct. Accordingly, in alternative embodiments of the present invention, an ECB method includes a combination of ECB irradiation and additional intravascular He—Ne irradiation of the blood.

In alternative embodiments of the present invention, an ECB method includes in vitro ECB irradiation of cells taken from skeletal muscle or embryonic heart muscle (cardiomyocytes) prior to their implantation into ischemic areas of the heart muscle, in accordance with the methods described by Li and Morgan, cited above. The applicants believe that such biostimulatory irradiation of the cells may improve their overall viability and increase their implant survival rate due to the beneficial effects of the biostimulatory irradiation with respect to cell preservation under ischemic conditions. As described by Li and Morgan, such viable implanted cells are believed to improve the heart function.

There is thus provided in accordance with a preferred embodiment of the present invention, a method for biostimulation of a myocardial tissue including irradiating the myocardial tissue with a source of electromagnetic radiation which causes biostimulation of the myocardial tissue.

Preferably, the electromagnetic radiation is selected from the group consisting of infrared, visible light and ultraviolet radiation.

Preferably, irradiating the tissue includes irradiating after the myocardial tissue develops an infarct of a given size, such that irradiating the myocardial tissue causes a reduction in the size of the infarct, and/or such that irradiating the myocardial tissue causes regeneration of cardiomyocytes in the infarct, and/or such that irradiating the myocardial tissue preserves structure and activity of mitochondria in cardiomyocytes in the infarct, and/or such that irradiating the myocardial tissue preserves structure and activity of contractile proteins in cardiomyocytes in the infarct.

Preferably, the source of electromagnetic radiation includes a source of coherent light, most preferably a diode laser having a power output in the range of 5 mW–5 W and a wavelength in the range of 250–940 nm.

Preferably, irradiating the tissue includes a plurality of irradiations of the myocardial tissue with the source of electromagnetic radiation and/or irradiating myocardial tissue with the source of electromagnetic radiation for a duration of 0.5–15 minutes.

In a preferred embodiment of the invention, irradiating the tissue includes introducing a catheter into the heart, preferably through the aorta, positioning the catheter in proximity to a heart wall, and irradiating the myocardial tissue via a waveguide introduced by the catheter into the heart, wherein the waveguide is coupled to the source of radiation.

In another preferred embodiment, a therapeutic chemical compound is administered in conjunction with the irradiating. Preferably, the chemical compound includes administering fructose-1,6-diphosphate (FDP), or alternatively, a seleno-organic free radicals scavenger. Preferably, irradiating the tissue and administering the chemical alleviate a post-reperfusion injury.

In still another preferred embodiment, a myocardial revascularization procedure in conjunction with the irradiating, wherein performing the myocardial revascularization procedure preferably includes performing a revascularization procedure simultaneously with the irradiating.

Preferably, physiological signals are received from the tissue, wherein irradiating the tissue includes irradiating heart tissue in response to the signals received therefrom. Preferably, the physiological signals include mechano-physiological signals and/or electrophysiological signals.

Preferably, positioning the catheter includes tracking location coordinates of the catheter using one or more position sensors. Further preferably, positioning the catheter includes positioning the catheter responsive to a viability map, which indicates ischemic areas in the heart tissue. Alternatively or additionally, positioning the catheter includes positioning the catheter relative to a grid delineating a zone to be irradiated on a geometrical map of the heart and, preferably, marking irradiated locations on the grid.

Preferably, irradiating the tissue includes simultaneously irradiating an area of the heart wall substantially larger than a cross-sectional area of the waveguide.

In a preferred embodiment of the invention, irradiating the tissue via the waveguide includes expanding a radial dimension of the waveguide adjacent the tissue.

In another preferred embodiment, positioning the catheter includes pressing a flexible distal portion of the catheter against the heart wall so that the portion conforms to the wall, and wherein irradiating the tissue includes irradiating an area radially adjacent the distal portion. Preferably, irradiating the tissue includes irradiating a first elongate stripe on the heart wall adjacent the distal portion in a first position thereof, and irradiating a plurality of stripes generally parallel to the first stripe.

In still another preferred embodiment, the catheter is introduced into a coronary artery.

In yet another preferred embodiment, irradiating the heart tissue includes irradiating the heart epicardially, in addition to or instead of irradiating via the waveguide introduced by the catheter.

Preferably, non-myocardial tissues are at least partially exposed in a generally perpendicular direction to a lateral wall of the myocardial tissue, and irradiating the tissue includes placing an optical element coupled to the source of electromagnetic radiation onto the at least partially exposed non-myocardial tissues. Preferably, the non-myocardial tissues include chest muscles of a chest cavity and irradiating the tissue includes placing the optical element into the chest cavity in a vicinity of the tissue, most preferably in proximity with the pleural membrane.

In a preferred embodiment of the invention, the source of electromagnetic radiation includes a source of concentrated non-coherent light, preferably a xenon lamp, most preferably having an radiative power flux of 30–500 mW/cm$^2$.

There is further provided, in accordance with a preferred embodiment of the present invention, apparatus for biostimulation of myocardial tissue including:
a source of electromagnetic radiation; and
relay optics, which receive the electromagnetic radiation, and convey the radiation to irradiate an ischemic area of the myocardial tissue.

In a preferred embodiment of the invention, the apparatus includes an echo transducer which communicates with an echo imaging device, the echo transducer being operative to provide positional information of the infarct; and a fastener which fastens the relay optics together with the echo transducer and which substantially maintains the two in a fixed spatial relationship with each other.

Preferably, the electromagnetic radiation source includes a coherent source, most preferably a diode laser having a power output in the range of 5 mW to 5 W and a wavelength in the range of 250 to 940 nm.

Alternatively, the electromagnetic radiation source includes a non-coherent source, preferably a xenon lamp having a radiative power flux of 30 to 500 mW/cm$^2$.

In a preferred embodiment of the invention, the apparatus includes a moving arm which holds the relay optics and a servo unit for controllably moving the arm.

Preferably, the relay optics include a fiberoptic light guide, having a distal end for introduction into a patient's chest, and a proximal end communicating with the electromagnetic radiation source. Preferably, the optics include a filter to attenuate electromagnetic radiation power output therefrom and a lens coupled to the distal end of the fiberoptic light guide.

In a preferred embodiment of the invention, the apparatus includes an elongate probe for introduction into a heart chamber, wherein the relay optics include a waveguide contained within the probe.

Preferably, the probe includes at least one position sensor, which is used to locate the probe within the chamber of the heart, wherein the position sensor preferably includes a magnetic position sensor, which generates signals responsive to an external magnetic field.

Additionally or alternatively, the probe includes at least one physiological sensor for sensing local physiological signals from the heart indicative of myocardial viability.

Further additionally or alternatively, the probe includes a radiometric sensor for sensing a local electromagnetic radiation power level reaching the myocardial tissue.

In a preferred embodiment of the invention, the probe includes a LMR waveguide, which communicates with a laser source for laser revascularization of the myocardial tissue. Preferably, the LMR waveguide is connected at its distal end to a lens adapted to concentrate the laser beam onto the tissue.

Preferably, the waveguide includes fiberoptics and is connected at a distal end thereof to an optical element, which spreads the biostimulatory electromagnetic radiation.

Preferably, the optical element includes a wide-angle lens, most preferably a fish-eye lens. Preferably, the optical element emits a beam having a cross-sectional area substantially larger than a cross-section of the waveguide.

There is also provided, in accordance with a preferred embodiment of the present invention, apparatus for intracardiac irradiation, including:
an elongate probe having a proximal end and a distal end for insertion into the heart of a subject, and including:
a waveguide, which conveys electromagnetic radiation from a source at the proximal end to the distal end; and
an optical element adjacent to the distal end, which receives electromagnetic radiation through the waveguide and emits a beam having a cross-sectional area substantially larger than a cross-section of the waveguide.

Preferably, the optical element includes an elongate, longitudinally-disposed element, which emits the beam in an outward radial direction relative to the probe.

Preferably, the optical element includes a curved outer surface and is at least 2 cm long and between 2 and 3 mm wide.

In a preferred embodiment of the invention, the probe includes a flexible portion, which contains the optical element, and which conforms to a wall of the heart such that the optical element is in physical contact therewith, wherein the probe preferably includes two or more proximity sensors, most preferably pressure sensors, which sense a contact of the probe with the heart wall.

In another preferred embodiment; the optical element includes a generally elliptical radiation-emitting area at the distal end of the probe, obliquely disposed with respect to the probe's longitudinal axis, wherein the element preferably has a convex outer surface.

In yet another preferred embodiment, the optical element includes a widening optical tip at the distal end, having a narrow, closed configuration for insertion into the heart and a wide, expanded configuration for irradiation of the myocardial tissue inside the heart.

Preferably, the tip includes a radiation scattering membrane. Alternatively or additionally, the tip includes a foldable reflector encompassing a radiation emitting point source, wherein the reflector preferably includes a multifaceted reflector.

Further alternatively, the tip includes a foldable fiberoptic bundle.

In a preferred embodiment of the invention, the probe includes an external sleeve and an internal sleeve, slideable within the external sleeve, wherein the internal sleeve includes a stretchable portion adjacent the distal end of the probe, which is held within the external sleeve in the closed configuration, and which stretches open when the internal sleeve is slid distally out of the external sleeve in the open configuration.

The present invention will be more fully understood from the following detailed description of the preferred embodiments thereof, taken together with the drawings in which:

BRIEF DESCRIPTION OF THE DRAWINGS

FIG. 2B is a simplified pictorial illustration of apparatus for ECB, constructed and operative in accordance with a preferred embodiment of the present invention;

FIGS. 7A and 7B are schematic illustrations of a catheter having a widening optical tip, in closed and open configurations, respectively, in accordance with a preferred embodiments of the present invention;

FIGS. 8A and 8B are schematic illustrations of a catheter having a widening optical tip, in closed and open configurations, respectively, in accordance with an alternative preferred embodiment of the present invention;

FIG. 8C is a schematic, cross-sectional illustration of the catheter of FIG. 8B:

DETAILED DESCRIPTION OF PREFERRED EMBODIMENTS

Figure 1:
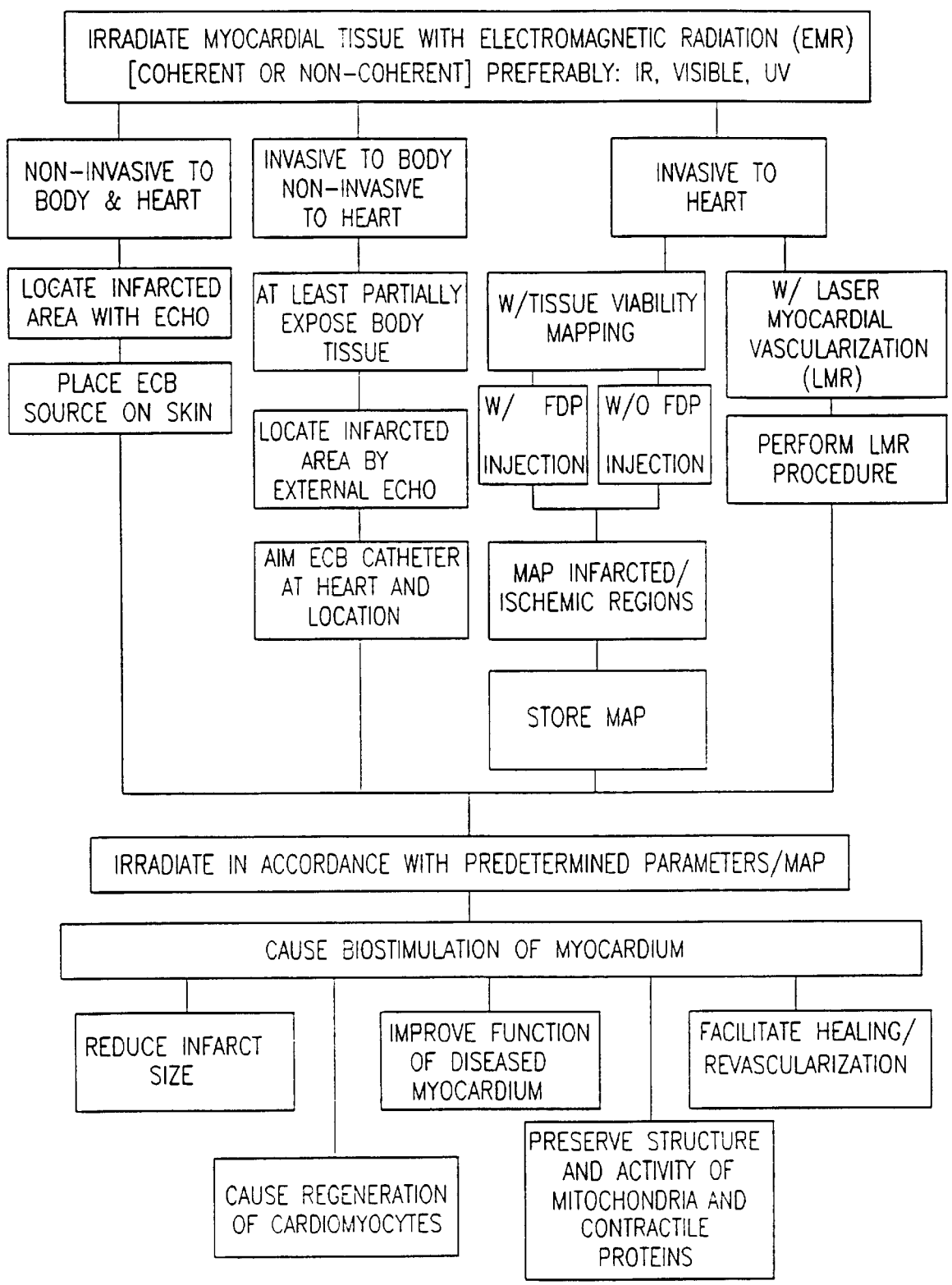
FIG. 1 is a chart illustrating alternative methods of ECB and their therapeutic effects, in accordance with preferred embodiments of the present invention.

Reference is now made to FIG. 1, which is a chart illustrating methods of electromagnetic cardiac biostimulation (ECB), in accordance with preferred embodiments of the present invention. These methods are based on irradiating the myocardial tissue with a source of electromagnetic radiation, which causes biostimulation Of the myocardial tissue. The methods are not limited to any particular range of wavelengths. However, the best mode of carrying out the invention is in the range including IR, visible light and UV radiation. The choice of which particular wavelength, power level, duration of irradiation and number of irradiation sessions is made in accordance with the patient's needs.

As will be described hereinbelow, the radiation may be coherent, such as radiation provided by a laser, or may alternatively be non-coherent, such as provided by a xenon lamp. The method may be non-invasive both to the body and to the heart, such as by placing a radiation transducer on the outer skin of the patient and irradiating the myocardium therefrom. Alternatively, some body tissue, such as non-myocardial muscle tissue, may be at least partially exposed, such as on the chest or back of the patient, and the transducer used to irradiate the heart therefrom. Although this option is partially invasive to the body, it has the advantage of allowing the irradiation to penetrate through a thinner muscle layer and attaining a higher and optimal radiative power on the heart muscle. Still alternatively, the method may be invasive to the heart, such as by irradiating the heart by means of a catheter introduced into a coronary artery or through a blood vessel, such as the aorta, into a chamber of the heart. Alternatively, the method may be invasive to the chest cavity, such as by introducing an optical fiber into the chest cavity and irradiating the heart muscle directly from within the chest cavity.

The irradiation causes biostimulation of the myocardium, as will be described in further detail below. For example, by irradiating the myocardial tissue after the development of an infarct, the irradiation may cause a reduction in the size of the infarct, may cause regeneration of cardiomyocytes in the infarct, may preserve structure and activity of mitochondria and contractile proteins in cardiomyocytes in the infarct and prevent their rapid degeneration after onset of myocardial infarct or ischemia, and/or may improve function of diseased myocardium.

In accordance with a preferred embodiment of the present invention the ECB is performed during and along with a laser myocardial revascularization (LMR) procedure, as will be described below in relation to FIGS. 4A and 4B.

In accordance with some preferred embodiments of the present invention, the irradiation is performed in conjunction with injection of drugs, most preferably FDP, as described above, injected before irradiation. Such injection is believed to partially inhibit (acute and post-infarct) ischemia by re-activating anaerobic glycolysis, and also to alleviate post-reperfusion injury, by accelerating the replenishment of high energy metabolites such as ATP and CP. The combination of ECB with the cytoprotective agent FDP is believed to be substantially synergetic with respect to healing effects on infarcted regions. Optionally, other cytoprotective drugs, for example, non-toxic seleno-organic free radical scavengers, may be used in combination with ECB to achieve such synergetic healing effects.

It will be appreciate that the specific treatment modalities illustrated in FIG. 1 are not intended to limit the scope of the present invention, but rather to summarize certain preferred embodiments. Those skilled in the art will understand that aspects of ECB treatment shown in the figures and described herein may be employed together in different combinations, as well as in combination with other methods and apparatus for cardiac treatment, as are known in the art.

EXPERIMENTAL RESULTS

Several experiments were carried out in accordance with alternative preferred embodiments of the present invention, and the results of these experiments are now summarized.

Experiment I

Forty-nine male Sprague-Dawley ether-anesthetized rats, 6–8 weeks old (220–260 g body weight) were used for the experiments. Two-cm incisions to the left of and parallel to the sternum were made; the fifth and sixth ribs were separated with a clamp, and the hearts were exteriorized by applying pressure to the lateral aspects of the thoracic cage.

The left coronary arteries were then occluded 2–3 mm from their origins with single sutures. The chests were closed and the rats allowed to recover. This procedure induces myocardial infarction (MI) and chronic ischemia.

Twenty-three rats were irradiated immediately following surgery using a diode laser (wavelength 780 nm; 38 mW). The irradiation was performed by placing and gently pressing a laser source tip onto the exposed intercostal muscles approximately in a perpendicular direction to the lateral wall of the left ventricle. The laser source was moved at a constant velocity for 2 min to cover the chest area from the sternum laterally to the left and between the 4th and the 8th rib in a medial-lateral direction.

In a separate experiment the efficiency of the laser penetration through the intercostal muscles of the rat (about 2 mm thick) was determined by placing the laser source as above and measuring the laser power with a special laser meter inserted in the chest cavity underneath the laser source. The laser power was at least 6 mW which is approximately the power that reaches the heart muscle.

Laser irradiation was repeated in the same way on the 3rd day post-operatively but for 3 min under light ether anesthesia. Control- rats were sham operated as the above-treated (laser irradiated) rats but were not exposed to laser irradiation. All the rats were ether-anesthetized at 21 days post-operatively, the chest opened and the heart (while beating) excised and immediately washed to remove blood by soaking in ice-cold saline for about 5 sec. The heart was then transversely cut into three equal parts (about 2 mm) from its apex. The middle section was fixed in neutral buffered formalin for 24 hr. The sections were dehydrated in alcohol embedded in paraffin and stained in Masson's trichrome.

The infarcted zone in each heart (the area where connective scar tissue was formed instead of contracting muscular tissue) was traced by differential staining of the scar tissue in Masson's staining. The infarct size was calculated in each section as a percentage occupied by, scar connective tissue out of the total area of the left ventricle. Quantitative morphometric measurement and statistics were performed as described previously in N. Weiss and U. Oron, ibid. and O. Barushka, T. Yaakobi and U. Oron, ibid.

The infarct size in the control rats was 29.6±4.3%; in the laser irradiated rats it included only 9.5±0.9%, significantly (P<0.001) lower than the infarct size in the control rats.

Possible adverse effects of the laser were investigated by irradiation of sham operated (heart exteriorized from the chest without coronary occlusion) rats compared to sham non-irradiated rats. The enzymatic activity of creatine phosphokinase (marker for cell viability) in the myocardium of both irradiated and non-irradiated rats was the same. No ultrastructural changes were observed in the myocardium of the irradiated rats as compared to control non-irradiated ones.

From the results of Experiment I, it is seen that laser irradiation after heart infarction causes about a 70% reduction of infarct size as compared to control non-irradiated rats. The mode of action of the low power laser on cells in general and cardiomyocytes in particular is not yet clearly understood. The marked reduction of infarct size by low power lasers and light may be of prime clinical importance. It may reduce the mortality in acute myocardial infarction in humans, especially in young people. It may also reduce the need for by-pass heart surgery following acute MI. It could also help to preserve the muscular tissue in hibernating (cooled) hearts separated from the blood circulation during open-heart or bypass surgery. Furthermore, it may improve the function of the heart muscle in various heart diseases (angina pectoris, for example).

Experiment II

Heart infarction was induced in 22 rats as described in Experiment I. Ten rats served as control and 12 rats underwent a different laser irradiation from that in Experiment I. The laser used was a diode laser with power of 47 mW and wavelength of 830 nm and irradiation was performed as described in Experiment I, but for 5 min immediately following induction of infarction. On the third and fourth day post-infarction, the rats underwent a further two sessions of laser irradiation under the same conditions as above. The rats were sacrificed after 21 days and the infarct size calculated as in Experiment I. The infarct size of control rats was 31±7%, whereas in the laser irradiated rats it comprised only 5.5±1.2% [significantly (p<0.001) lower than control]. The infarct size of the laser irradiated rats was also significantly smaller (p<0.05) than that of the laser irradiated rats in Experiment I.

From the results of Experiment II, it is seen that in various wavelengths (at least in the range of 700–830 nm), output power, time of irradiation (which determines the total energy given to the tissue) and timing after infarct induction of the beneficial effect of the laser irradiation on the infarcted heart is relevant. Moreover, the induction of the infarct size was even better in Experiment II than in Experiment I.

Experiment III

Heart attacks were induced in another group of 21 rats as described in Experiment I. Ten rats served as control and 11 rats underwent the laser treatment as described in Experiment I. After 21 days post induction of heart attack, the hearts were removed and connected to a Langendorff apparatus in an artificial physiological solution. They were then injected with TTC (triphenyltetrazolium chloride) through the coronary arteries. This solution stains "healthy" uninjured heart cells with red and injured scar tissue in the heart with a pale yellow color. The hearts were then fixed in neutral buffered formalin and sectioned transversely. Quantitative morphometric measurements and statistics were performed as in Experiment I.

The infarct size (injured pale yellow area as percent of total area of the left ventricle) was 32±5% in the control group which was significantly (P<0.01) higher than laser irradiated group which comprised 8±3%.

Experiment IV

Heart infarction was experimentally induced in 24 rats as described in Experiment I. Twelve rats were laser-irradiated as in Experiment I, and 12 rats served as control. At 6 and 21 days post-experimentally induced infarct, 6 control and 6 laser-irradiated rats were sacrificed, and histological sections from the heart were prepared as in Experiment I. The sections were stained with antibody to desmin in order to trace cells which synthesize newly-formed myogenic contractile proteins. As is known in the art, desmin is a protein which serves as a marker for embryonic muscle cells. Desmin is only found in the cytoplasm of cells that synthesize myogenic contractile proteins. It was found that many cells in the infarct zone in the laser irradiated rats were positively stained to desmin whereas in the non-irradiated rats there was almost no staining for desmin.

It is seen from Experiment IV, that laser irradiation may be used to induce formation of new regenerative heart cells or synthesis of new contractile proteins in partially injured cells in the infarcted area. This embodiment of the present invention is an important medical discovery and is a radical departure from current art, in which it is not known how to induce regeneration of cardiomyocytes.

Experiment V

The same experimental system was used as in Experiment I (induction of MI in rats). Twenty rats underwent the procedure for creating MI in the myocardium of the left ventricle. Ten rats served as control sham operated rats, while another ten rats were irradiated immediately following surgery with concentrated light produced by a xenon lamp. The output intensity of the light source was about 250 mW/cm$^2$. The light beam (about 2 cm in diameter) was aimed directly at the intercostal exposed and partially cut chest muscles (in order to allow better penetration of light to the chest cavity and heart) above the location of the heart for 10 min. Light irradiation was repeated as above also during the second and fourth days post infarction, once a day. At 21 days post-operatively, the hearts of both control and light-irradiated rats were exposed and treated for measurement of infarct size as in Experiment I. The infarct size was 32±6% in the control rats, compared with 22±4% in the light-irradiated rats. There was a 30% significant ($P<0.05$) reduction in infarct size in the light irradiation rats.

It is seen from Experiment V that not only coherent laser irradiation, but also concentrated light, can cause a significant reduction in infarct size.

Experiment VI

Sarafotoxin, a component of snake venom that acts like endothelin, is known to induce contraction of smooth muscle and to cause, when injected into the bloodstream of mice at a certain dose, ventricular fibrillation, ultimately resulting in the death of the injected subject due to heart failure similar to that observed in cases of heart attacks.

Three groups of 10 mice each, were used in an experiment for investigating the effects of biostimulatory radiation in conjunction with sarafotoxin intoxication as. follows: group I, which served as a control group, was injected with saline solution through the tail vein; groups II and III were injected with sarafotoxin at a dose that causes death of 50% of the injected population within one hour. Group III was irradiated immediately following the injection of sarafotoxin similarly to the rats in Experiment I and again two days thereafter. All mice were sacrificed 7 days after the injection of sarafotoxin.

Upon examination, heart ventricles of sarafotoxin-injected mice were found to be significantly dilated as compared to the control. Electron microscopy analysis showed damage to myocardial cells of the dilated ventricles. In particular, it revealed swollen vacuoles containing cardiomyocytes with disorganized contractile apparatus and other cell organelles. ECG analysis showed possible damage to the conducting system in the hearts of injected mice.

The dilatation index, defined as the ratio (in percent) of left ventricular cavity to total volume of left ventricle, of non-irradiated sarafotoxin injected (group II) mice was 22±7%. In the laser-irradiated (group III) mice the dilatation index was 12±8%, significantly ($p<0.05$) lower than in the non-irradiated mice. Moreover, the cardiomyocytes of the irradiated mice showed a more organized contractile apparatus and contained fewer vacuoles.

From the results of Experiment VI, it is concluded that the laser irradiation, as applied in the experiment, protects the cardiomyocytes and probably the conducting system, as well, from the adverse effects of sarafotoxin. It will thus be appreciated that in addition to the therapeutic effects of ECB in treating ischemic and infarcted heart tissue, as shown by Experiments I–V above, ECB is also effective in counter-acting cardiotoxic effects.

Experiment VI

Two groups of 9 rats each, were used in an experiment for investigating the effects of biostimulatory radiation under circumstances of post-infarct reperfusion, believed to involve formation of superoxides and post-reperfusion injury. Myocardial infarction was induced in all 18 rats, as in Experiment I, with the exception of leaving one end of the suture used for occluding the left coronary artery (LAD) accessible within the chest muscle, to enable later release of the occlusion. Group I of nine rats was irradiated immediately following the occlusion, similarly to the rats in Experiment I. Group II served as a control, sham-operated group, and the rats of this group were not irradiated following the occlusion. Forty-five minutes after the occlusion, the suture end was pulled, and the occlusion of the LAD was thus released, resulting in reperfusion of the ischemic area. All rats were sacrificed after 14 days, and their hearts processed for histology as described in Experiment I. The dilatation index (as defined above in Experiment VI) of laser-irradiated (Group I) rats was 0.1+/−0.06, which was significantly ($p<0.05$) lower than that of the non-irradiated (Group II) rats (0.18+/−0.02).

Experiment VII simulates situations of post-infarct reperfusion (i.e., reperfusion of ischemic areas), involving superoxide formation and post-reperfusion injury, such as may be encountered upon release of an obstruction within a coronary artery by balloon angioplasty or drug treatment, for example. The results of Experiment VII indicate that the biostimulatory laser irradiation, as applied in the experiment, has a beneficial effect with respect to post-reperfusion injury, as shown by the relative reduction in the dilatation index of the ventricular cavity.

Experiment VIII

Thirteen rats were used in an experiment for investigating the effect of laser power output in biostimulatory radiation of ischemic heart zones. The same experimental system was used as in Experiment I (induction of MI in rats). Six rats served as control, sham-operated rats, while another seven rats were irradiated immediately following surgery with laser light of similar wavelength as in Experiment I and a power output of 220 mW. The residual power level measured after passage of the radiation through the chest muscles, corresponding to the laser power level reaching the irradiated heart tissue, was 28–30 mW, six times higher than the power levels employed in Experiment I. All rats were sacrificed after 14 days, and their hearts analyzed for infarct size, as described with reference to Experiment I. The infarct size of the laser irradiated rats was 37±8%, and that of the control (sham-operated, non-irradiated) rats was 39±6.5%, not significantly different from the irradiated rats.

The results of Experiment VIII indicate the possible existence of optimal laser power levels with respect to biostimulatory effects on infarcted heart zones. Since a six-fold increase in the power level had practically no effect on the infarct size, as opposed to the significant reduction in infarct size observed in the earlier experiments employing lower power levels, it appears that above a certain level, the efficacy of the biostimulation drops off with increasing power.

APPARATUS AND METHODS FOR ECB

Figure 2A:
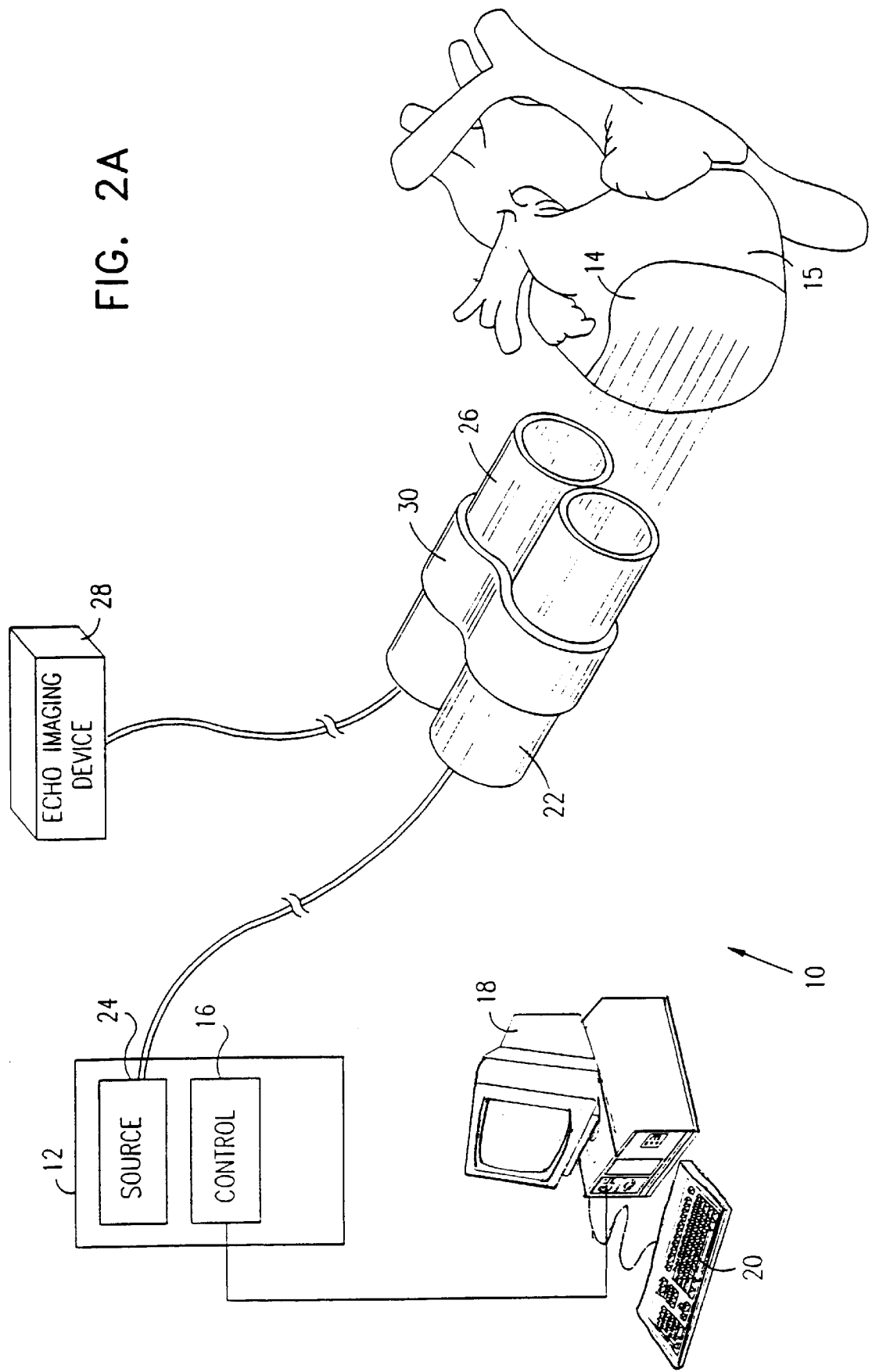
FIG. 2A is a simplified pictorial illustration of apparatus for ECB, constructed and operative in accordance with a preferred embodiment of the present invention.

Reference is now made to FIG. 2A, which illustrates apparatus 10 for biostimulation by electromagnetic radiation of a myocardial tissue, denoted in the context of the present application and claims as ECB apparatus. Apparatus 10 preferably comprises a console 12 comprising a control circuitry 16 which, inter alia, may control duration and power level of irradiation, automatically switch-off the irradiation at the end of treatment, generate operational information to be displayed on a display 18, and allow adjustment of operational parameters during treatment via a control interface, for example, a keyboard 20. The apparatus further comprises electromagnetic radiation relay optics 22, which communicate with a source 24 of electromagnetic radiation, such as a laser source. Optics 22 transmit radiation from source 24 onto an infarct 14 of a myocardial tissue 15 when suitably positioned. Optionally, optics 22 is placed against partially exposed non-myocardial tissue on the chest or back of the patient.

Preferably, apparatus 10 includes an echo transducer 26, which communicates with an echo imaging device 28. Echo transducer 26 is used to produce an ultrasound image, which provides positional information regarding infarct 14. A fastener 30 fastens optics 22 together with echo transducer 26 and substantially maintains the optics and the transducer in a fixed spatial relationship with each other. Fastener 30 may be any type of band. clamp, housing or bracket, for example, and may be made of any suitably stiff material, such as metal or plastic. Echo transducer 26 may be used to monitor the position and size of infarct 14 while simultaneously infarct 14 is irradiated via optics 22.

Source 24 preferably comprises a laser unit powered by a suitable power supply. This laser unit preferably includes a multiplicity of diode lasers, pulsed or continuous, with a preferable wavelength in the range of 630 to 940 nm and a total modulated power output of 5 mW to 5 W. Alternatively, source 24 may comprise a non-coherent source, such as a broad-band xenon lamp or a UV source, for example.

The diode lasers are preferably spaced 0.5–1 cm from each other and mounted on a base. The base is preferably arcuate in shape and may be constructed of a suitably sturdy material, such as various plastic materials, or steel. Typically, the base may be 5 to 50 cm in length and 20 cm wide, with 60–100 diode lasers mounted thereon. The laser unit is preferably provided with means which allow for external control of its operational parameters.

Another example of radiation source 24 is a laser unit comprising a plurality of preferably portable, versatile (continuous or pulsed) diode lasers or any other (e.g., He—Ne) laser sources at modulated wavelengths, 639 to 940 nm, with a modulated power output of 40 mW to 5 W, and a modulated beam diameter.

Source 24 or optics 22 may be further provided with an automated scanning device, for example an automatically controlled lever arm. The lever arm is preferably mounted on an adjustable telescopic electric support having "all-direction" wheels. A scanning device of this sort is shown below in FIG. 2B with respect to another preferred embodiment of the present invention.

FIG. 2B illustrates apparatus 32 for partially invasive ECB, in accordance with another preferred embodiment of the present invention. Apparatus 32 preferably comprises, in addition to the units described with reference to apparatus 10 of FIG. 2A above, a fiberoptic waveguide 34, which is connected to electromagnetic radiation source 24. It further comprises a servo unit 42, including a moving arm 44 and a rigid sleeve 46, which protects waveguide 34 from mechanical damage. Waveguide 34 comprises, preferably at its distal end 36, a filter 38 for attenuating the radiation output power and a lens 40. During partially invasive ECB, distal end 36 of waveguide 34 is inserted into a patient's body through an incision in the chest. An interventional cardiologist or surgeon moves the waveguide by means of moving arm 44 until it reaches the inner pleural membrane. The lens 40 is positioned in close proximity to the pleural membrane and the biostimulatory radiation is aimed at ischemic regions of the myocardium through the pleural membrane, which functions as a radiation-diffusing optical membrane, spreading the radiation beam emitted from the lens 40 over a wide target area.

Figure 3A:
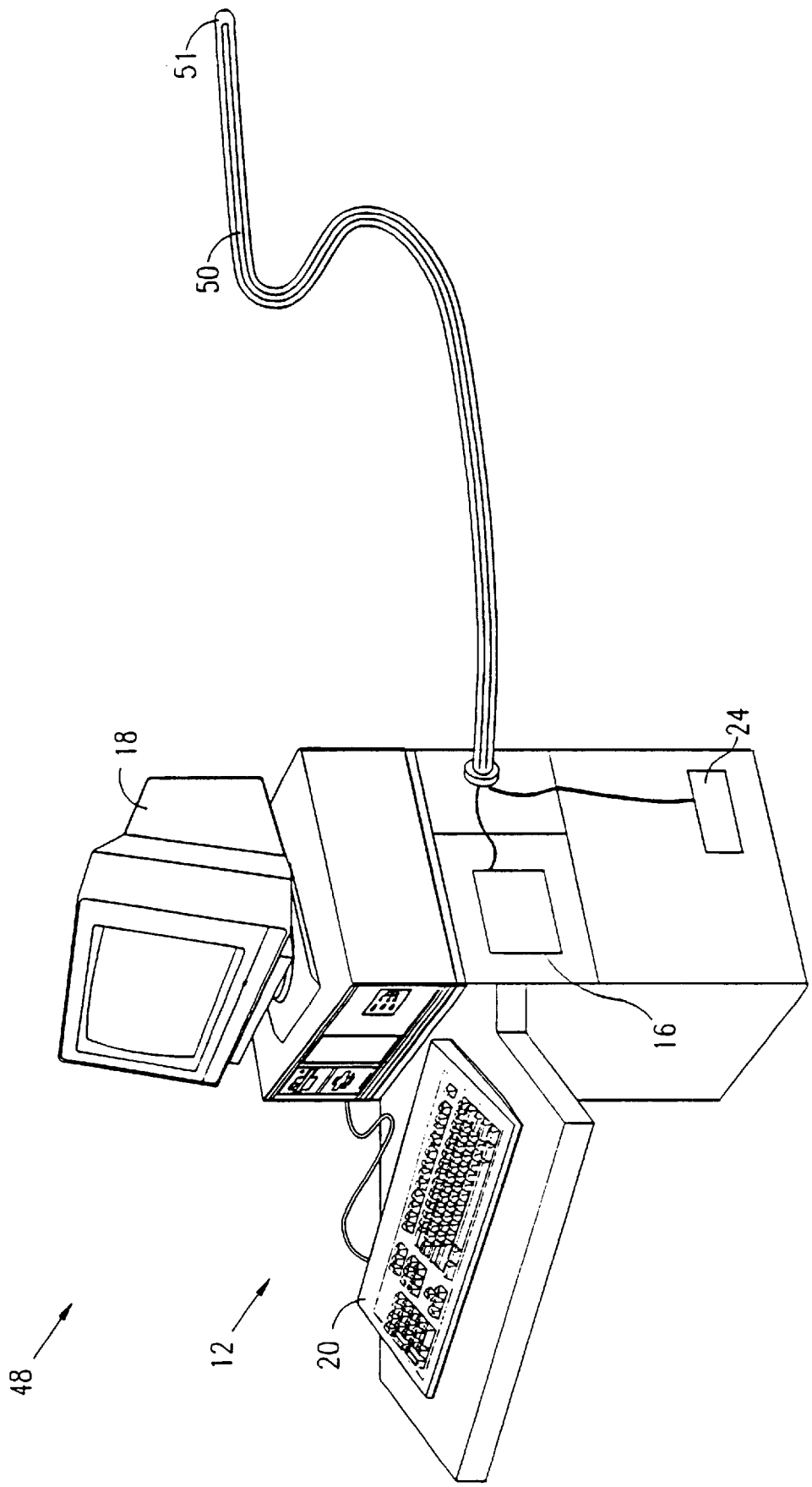
FIG. 3A is a simplified pictorial illustration of ECB apparatus, in accordance with another preferred embodiment of the present invention.

FIG. 3A is a schematic, pictorial illustration showing apparatus 48 for invasive intracardiac ECB treatment, in accordance with another preferred embodiment of the present invention. Apparatus 48 preferably comprises, in addition to the units described with reference to apparatus 10 of FIG. 2A above, a catheter 50 for insertion into a chamber of the heart (shown in detail in FIG. 3B below and described with reference thereto) and connected to electromagnetic radiation source 24 and control circuitry 16.

Figure 3B:
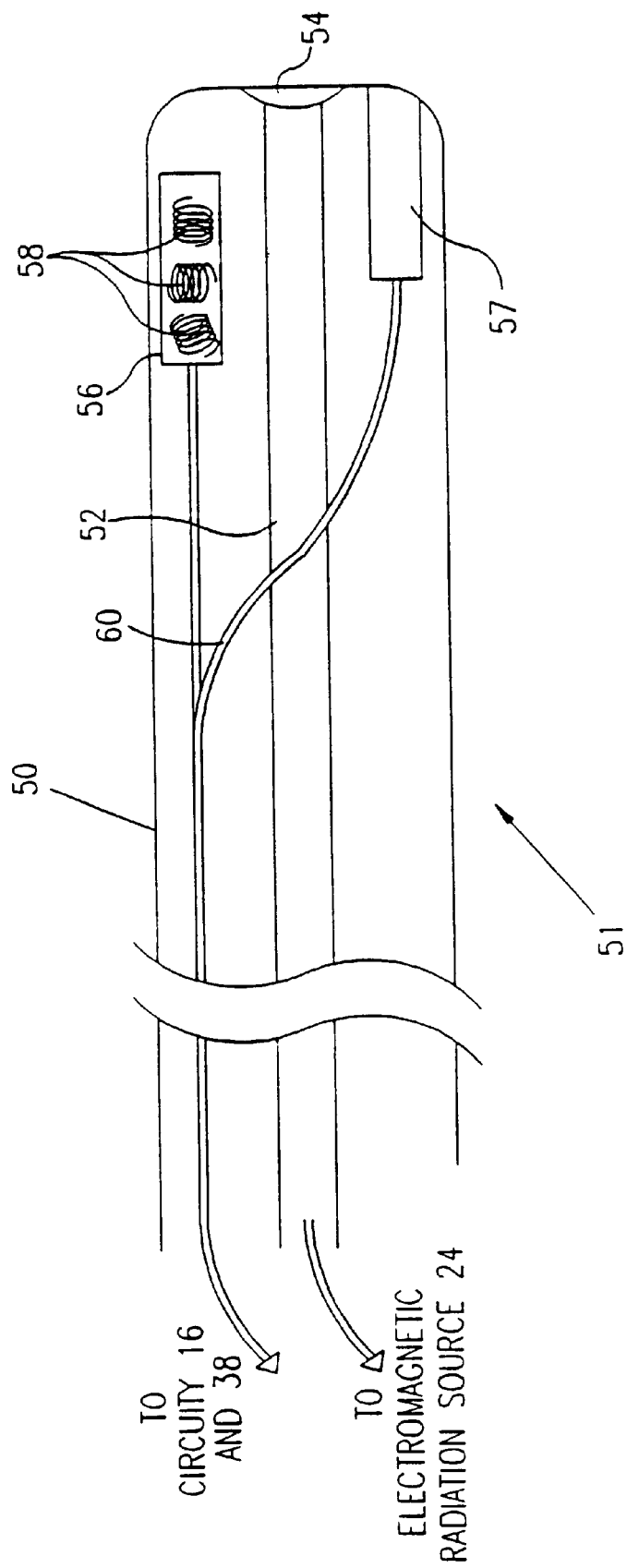
FIG. 3B is a schematic illustration of an ECB catheter, in accordance with a preferred embodiment of the present invention.

FIG. 3B is a schematic, detail view of a distal portion 51 of catheter 50. Catheter 50 comprises a waveguide 52 connected proximally to electromagnetic radiation source 24 and distally to lens 54. It further comprises a position sensor 56, preferably comprising magnetic coils 58 connected via wires 60 to circuitry 16, for determination of the position of distal portion 51 with respect to an externally-applied magnetic field, as described in the above-mentioned PCT publication WO96/05768. The catheter is navigated and located using the position sensor, preferably following a grid of points on a geometrical map of the heart muscle, marking ischemic zones to be irradiated. Preferably, the grid is determined based on a viability map of the heart, which is generated ahead of time using one of the methods described below, and is input to control circuitry 16. Alternatively, the generation of the viability map proceeds during and along with the ECB irradiation.

Optionally, the catheter includes a radiometric sensor 57, which is placed against the myocardium at a site to be irradiated. The radiometric sensor measures the actual radiation power level hitting the myocardium surface and the total energy supplied to the site during an ECB session. The power level and energy data may be employed to modulate the power level of source 24 or to ascertain proper location and orientation of the catheter during irradiation, as well as proper operation of the electromagnetic radiation source during the ECB session.

Figure 3C:
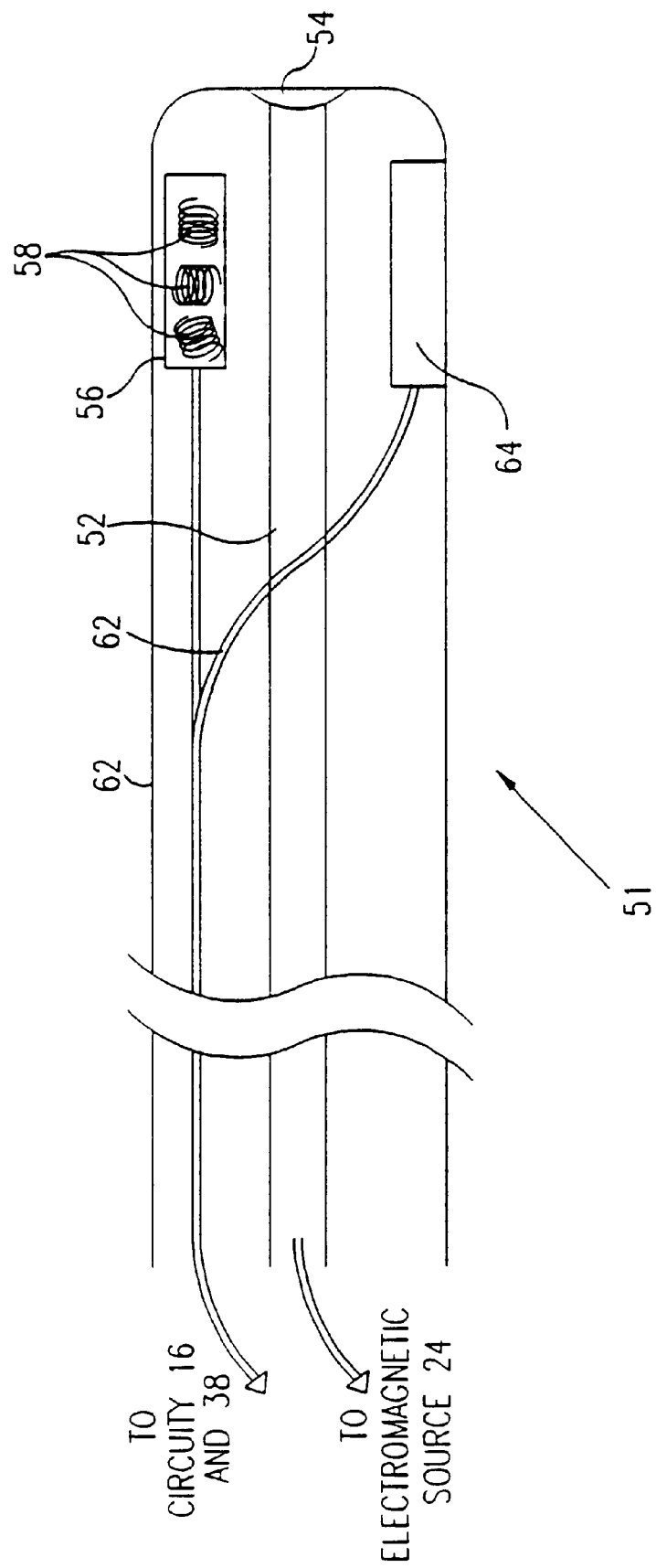
FIG. 3C is a schematic illustration of an ECB catheter, in accordance with another preferred embodiment of the present invention.

FIG. 3C is a schematic, detail view of distal portion 51 of a catheter 62 used in conjunction with apparatus 48 (shown in FIG. 3A above), in accordance with an alternative preferred embodiment of the present invention. In this embodiment, the ECB procedure is performed in combination and concomitantly with a viability mapping procedure. Accordingly, catheter 62 comprises at least one physiological sensor 64, which senses physiological signals from the heart responsive to local tissue viability. Such a viability map is useful in identifying ischemic but still viable areas of the heart tissue, to which ECB therapy could most usefully be applied, as opposed to infarcted and non-viable areas or to well-perfused and healthy areas, for which ECB would not be useful. For this purpose, sensor 64 preferably comprises an electro-physiological electrode which senses electrogram signals, or a mechano-physiological detector, sensing mechanical signals, as described, for example, in the above-mentioned U.S. patent application Ser. No. 08/595,365 and U.S. Pat. No. 5,568,809.

ECB radiation source 24 is operated in response to local viability data generated by sensor 64. Optionally, the viability data along with the location coordinates generated by position sensor 56 are used to generate a viability map of the myocardial tissue, together with and during the ECB irradiation. Preferably, a grid of points is selected and marked on the map, covering ischemic zones to be irradiated and indicating the points in the zones at which catheter 62 is to be positioned for this purpose. As the irradiation of the designated zones proceeds, the map is updated to identify the irradiated sites. Optionally, the viability detection procedure may be performed again post-irradiation to assess the efficacy of the treatment.

Figure 4A:
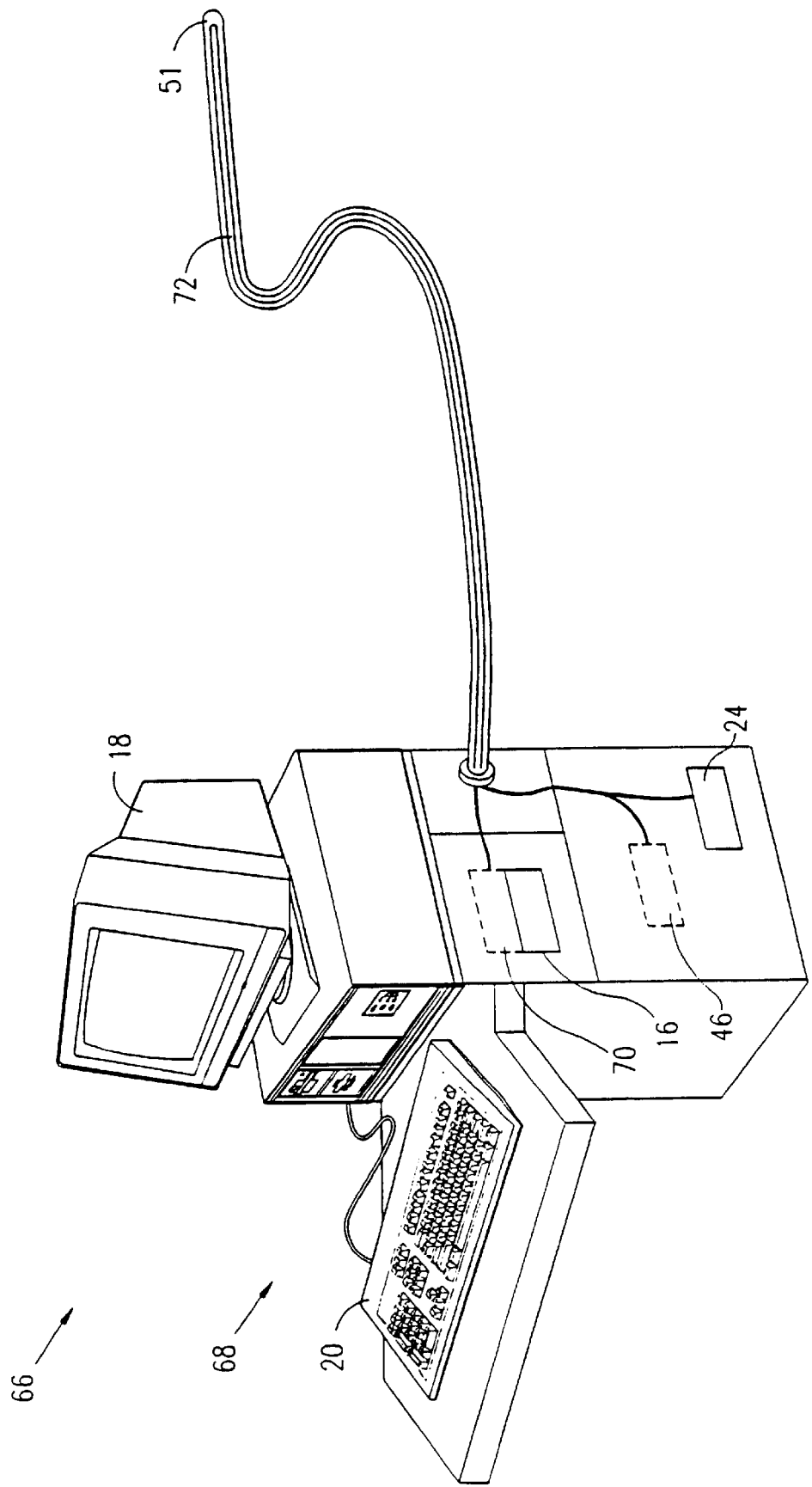
FIG. 4A is a simplified pictorial illustration of integrated ECB and laser myocardial revascularization apparatus, in accordance with a preferred embodiment of the present invention.

Though the above embodiment is described with respect to electro- or mechano-physiological detectors, other physiological detectors may be employed, as well, to provide tissue viability data, for example, perfusion detectors, which measure local microcirculation blood flow rate, or optical detectors, which sense fluorescent emission related to local blood perfusion, FIG. 4A is a schematic illustration showing apparatus 66 for combined LMR (laser myocardial revascularization) and ECB therapy, in accordance with another preferred embodiment of the present invention. Apparatus 66 comprises a console 68, including LMR control circuitry 70 and ECB control circuitry 16, a LMR laser source 46, electromagnetic ECB radiation source 24 and a catheter 72 for insertion into a chamber of the heart (shown in detail in FIG. 4B below and described with reference thereto). Catheter 72 comprises one waveguide 74 connected to laser source 46 and another waveguide 52 connected to electromagnetic radiation source 24. Preferably, the catheter also comprises position sensor 56, as described above.

Figure 4B:
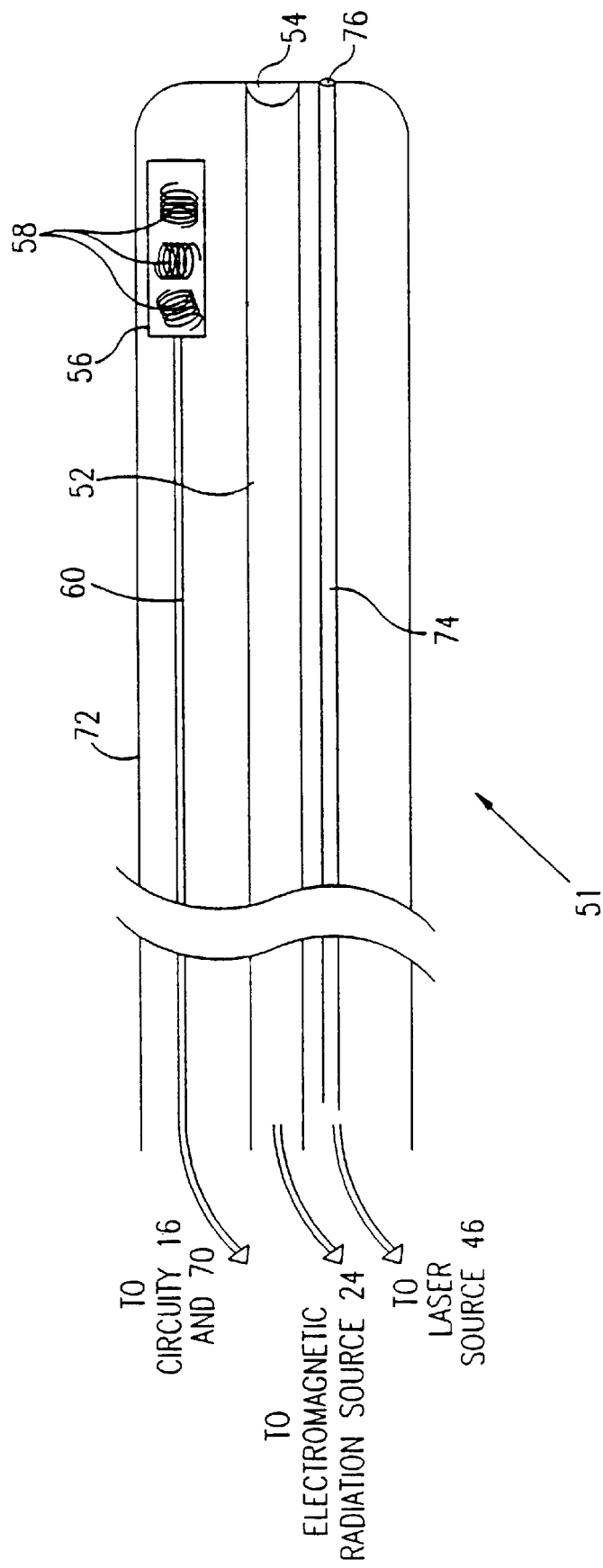
FIG. 4B is a schematic illustration of an integrated ECB and laser myocardial revascularization catheter, in accordance with an alternative preferred embodiment of the present invention.

FIG. 4B is a schematic illustration showing details of distal portion 51 of catheter 72, shown in FIG. 4A. The catheter is navigated to an ischemic region to be treated and is located as described below. Waveguide 52, which is coupled to electromagnetic radiation source 24, transmits the ECB electromagnetic radiation through lens 54 onto the ischemic region. Optionally, a single waveguide, connected to LMR laser source 46 and electromagnetic radiation source 24 transmits both beams, together or in succession, from the respective source through a single composite lens to the myocardial tissue. Since LMR source 46 preferably comprises a far-infrared laser, for example, a $CO_2$ laser, and ECB source 24 preferably comprises a visible radiation source, lens 76 can be suitably designed to concentrate the LMR beam and spread the ECB beam, for example, using diffractive optics, as are known in the art.

Catheter 72 is fed through a blood vessel, such as the aorta, into a chamber of the heart and navigated to an ischemic area by means of position sensor 56. At each of a grid of points in the ischemic area, designated on a map of the heart, as described above and in the above-mentioned PCT/IL97/00011 patent application, both LMR laser source 46 and biostimulatory irradiation source 24 are activated. The point that has been irradiated is then marked on the grid. The LMR radiation generates a revascularizing channel at each point. ECB irradiation of the generated channels and the surrounding ischemic region is believed to enhance the healing process and synergistically affect the ischemic or infarcted zone. Alternatively, the ECB irradiation is performed upon completion of all LMR channels, preferably following the same map. Optionally, the combined ECB/LMR procedure may be performed in conjunction with administration of FDP or non-toxic seleno-organic free radical scavengers, as described above.

Typically, ischemic zones may comprise up to 10 $cm^2$ of myocardium, whereas the typical cross-section of catheters 50, 62 and 72 is several $mm^2$. Moreover, the extinction coefficient of electromagnetic radiation of biostimulatory wavelengths in blood and muscular tissue is so high that the radiation does not penetrate more than a few millimeters through the blood or tissue. The steep decay in power level imposes the need for close proximity or, preferably, physical contact between the light emitting area of the catheter and the ischemic tissue. Accordingly, lens 54 preferably comprises a wide angle lens, for example, a fish-eye lens, as is known in the art, so as to widen the irradiation beam over a short focal distance and thus to reduce the number of different points at which the catheter must be repositioned in order to irradiate completely a designated area in the heart. In other preferred embodiments, described below, ECB catheters include specially-designed beam output optics, so as to increase the irradiated area still further.

Figure 5A:
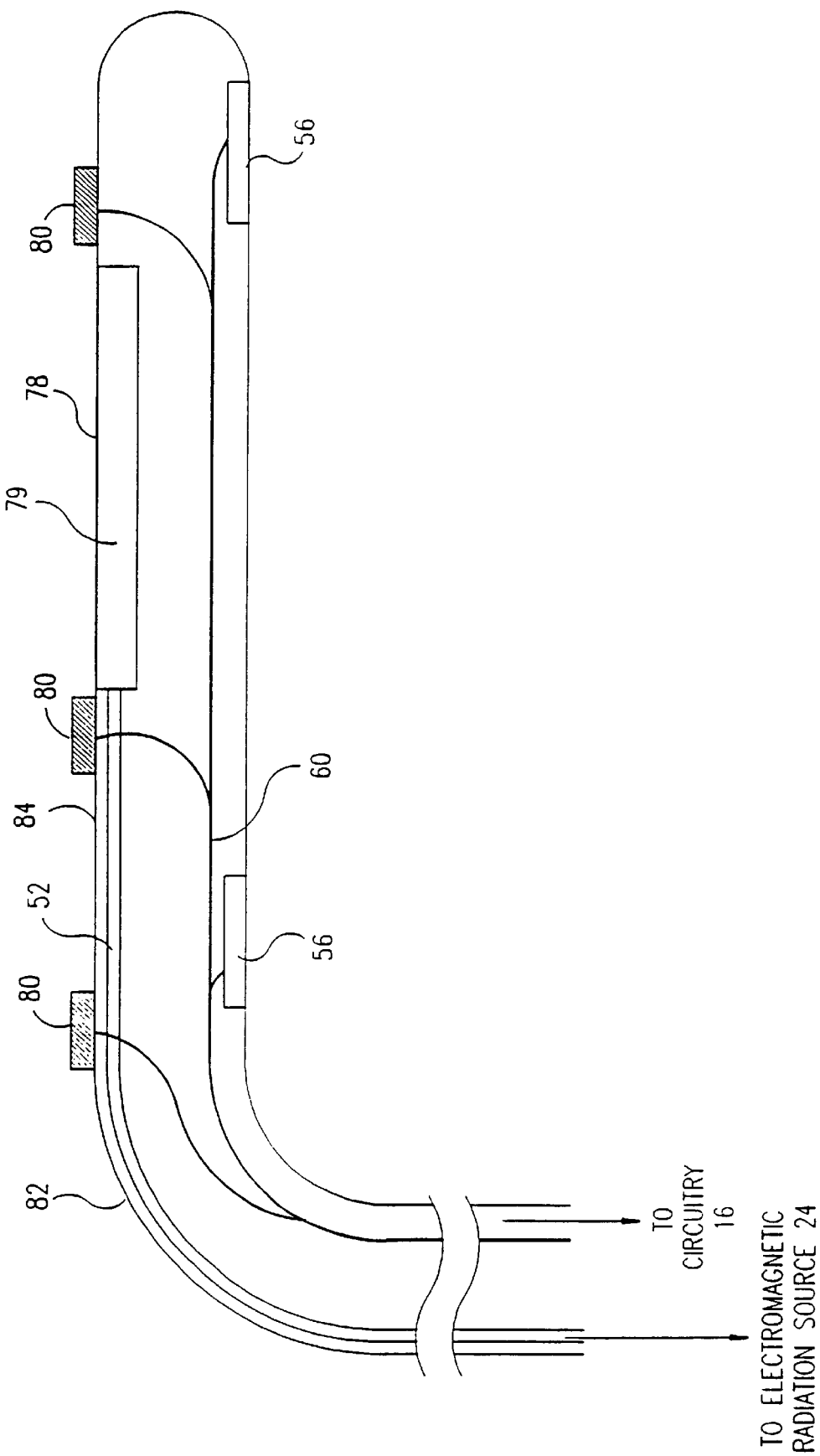
FIG. 5A is a schematic illustration of an ECB side-emitting catheter, in accordance with a preferred embodiment of the present invention.
Figure 5B:
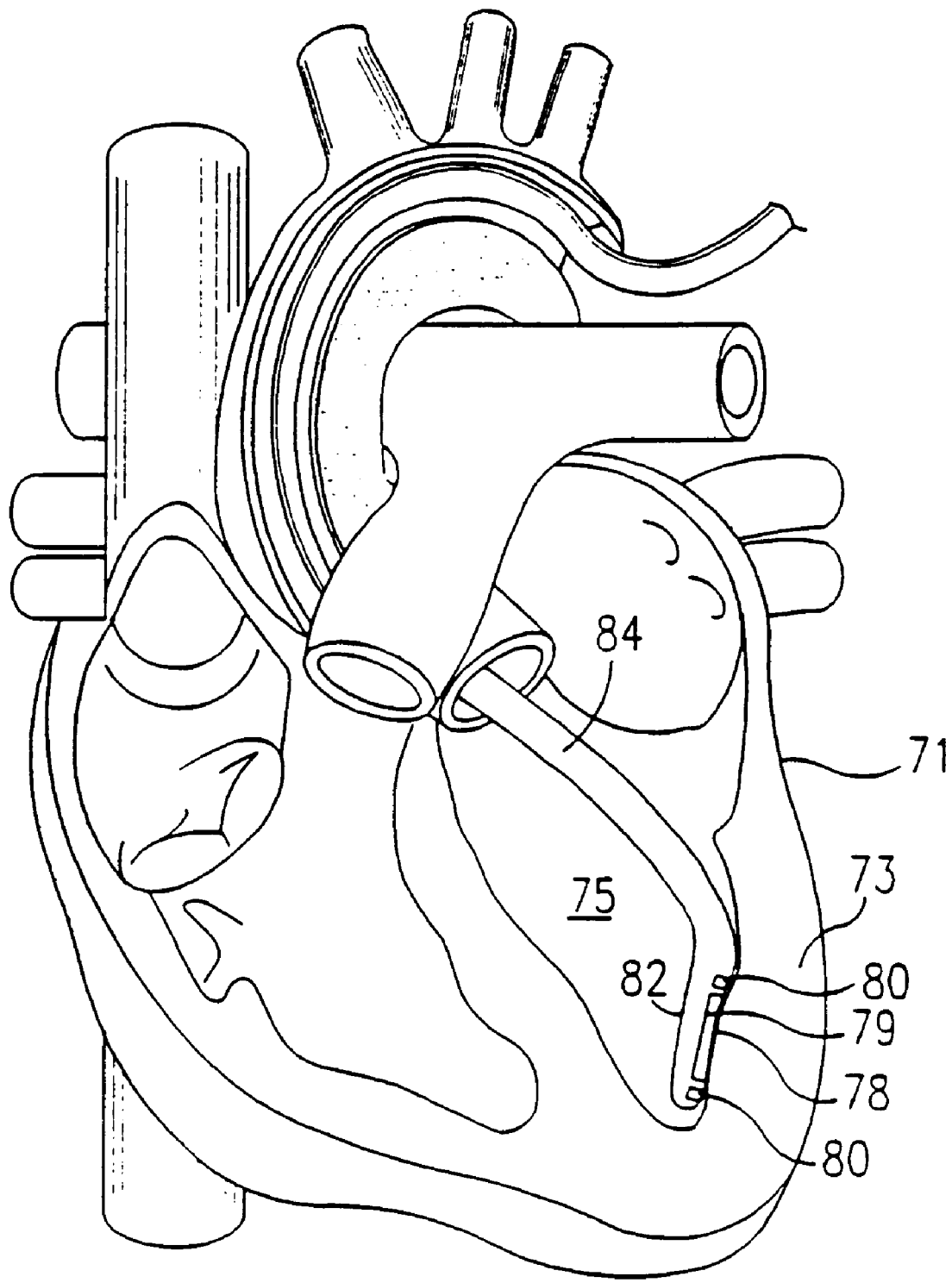
FIG. 5B is a schematic illustration showing the catheter of FIG. 5A inserted into the left ventricle of a heart, in accordance with a preferred embodiment of the present invention.

FIG. 5A schematically illustrates a catheter 84 for ECB therapy, in accordance with another preferred embodiment of the present invention. Catheter 84 comprises a flexible distal portion 82, which conforms to an inner surface of the heart wall when pressed thereagainst, as described in the above-mentioned U.S. Provisional Patent Application 60/034,704 and incorporated herein by reference. A plurality of pressure sensors 80 and at least two position sensors 56 are spaced along flexible portion 82 and are connected via wires 60 to circuitry 16. Sensors 56 and 80 are used to ascertain the position and, preferably, orientation of portion 82 against the heart wall. If the output signals of all sensors 80 are at roughly equal respective positive pressures, it may be assumed that flexible portion 82 is conforming to the shape of the internal heart wall (as shown in FIG. 5B and described with reference thereto). It will be understood that there may be a greater or lesser number of pressure sensors, and that other sensors, may be used to ascertain that portion 82 conforms to the heart wall, as described in detail in the 60/034,704 application.

Catheter 84 further comprises a longitudinally-disposed radiation emitting element 79, which preferably fits in a cutaway section 78 along the distal end of flexible portion 82. Radiation emitting element 79 is coupled to receive electromagnetic radiation via waveguide 52 from electromagnetic radiation source 24 (shown in FIG. 2B, for example), so as to irradiate cardiac tissue adjacent to the element. Element 79 may comprise a cylindrical lens, for example, having a curved outer surface which emits a beam of electromagnetic radiation preferentially in an outward, radial direction relative to catheter 84, whereas the inner surface of the lens is reflectively coated. Alternatively, element 79 may comprise a section of optical light guide or any other suitable optical element known in the art. Most preferably, cutaway section 78 is 2 to 3 cm long and 0.2 to 0.3 cm wide, forming a radiation emitting area of approximately 0.5 $cm^2$. It will thus be appreciated that the cross-section of the emitted beam is substantially larger than the cross-section of waveguide 52, so that for each position of catheter 84 against the heart wall, a substantial area of the heart tissue is irradiated.

FIG. 5B is a schematic illustration showing catheter 84 inserted into a ventricle 75 of heart 71. Flexible portion 82 of catheter 84 is pressed against an internal heart wall 73 and conforms to the shape thereof such that the output signals of all sensors 80 are at roughly equal respective positive pressures. Optics 79 is oriented towards the area to be irradiated and in physical contact therewith, such that attenuation of the emitted radiation beam due to inadvertent absorption by the blood in ventricle 75 is kept to a minimum.

Catheter 84 is preferably navigated and located using position sensors 56 and following the grid on the geometric map of the heart, as described in detail with reference to FIG. 3B above. Preferable, the catheter is located and oriented such that the coordinates of each of position sensors 50 located on flexible portion 82 correspond to a respective grid point on the map. In such a position, radiation emitting element 78 will contact and irradiate a "stripe" of known position and dimensions in the heart wall. The catheter is preferably successively repositioned to irradiate a series of parallel stripes, following the arid, thereby copying a designated region of heart wall 73. If desired, catheter 84 may then be reoriented along the grid at approximately right angles to this series of stripes, so as to irradiated a second series of stripes perpendicular thereto.

Figure 6:
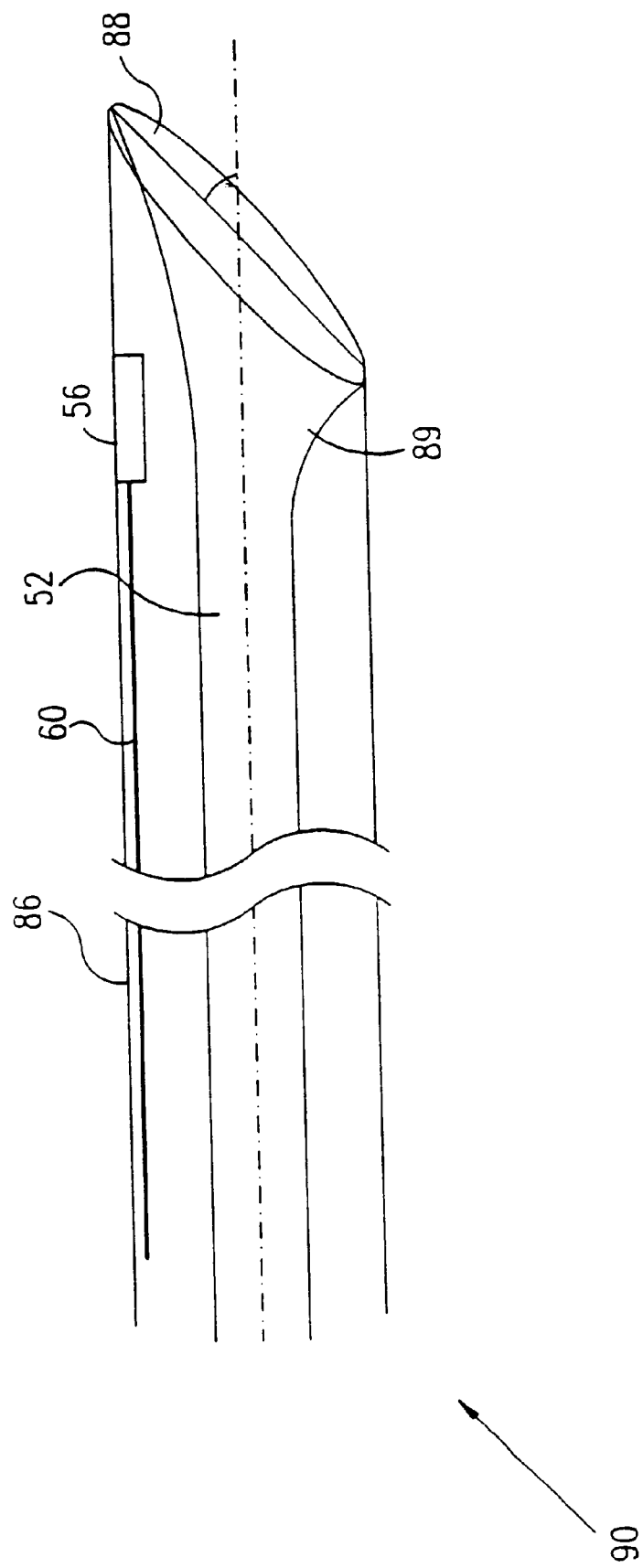
FIG. 6 is a schematic illustration of a section of a slant-tip catheter, in accordance with a preferred embodiment of the present invention.

FIG. 6 is a schematic illustration showing a distal section 90 of a slant-tip catheter 86, in accordance with another preferred embodiment of the present invention. Catheter 86 includes a generally elliptical radiation emitting area 88, angled with respect to the catheter's longitudinal axis and connected to waveguide 52 via a beam expander 89, which couples the narrow distal tip of waveguide 52 with the broader radiation-emitting area 88. Preferably, elliptical radiation emitting area 88 comprises a convex surface, for further increasing the radiation emitting area. Catheter 86 preferably includes position sensing and other functional elements described above (not shown in FIG. 6 for the sake of simplicity). It shares the advantage of catheter 84, shown in FIGS. 5A and 5B, that it enables a larger area of the heart wall to be irradiated for each point at which position.

Figure 7B:
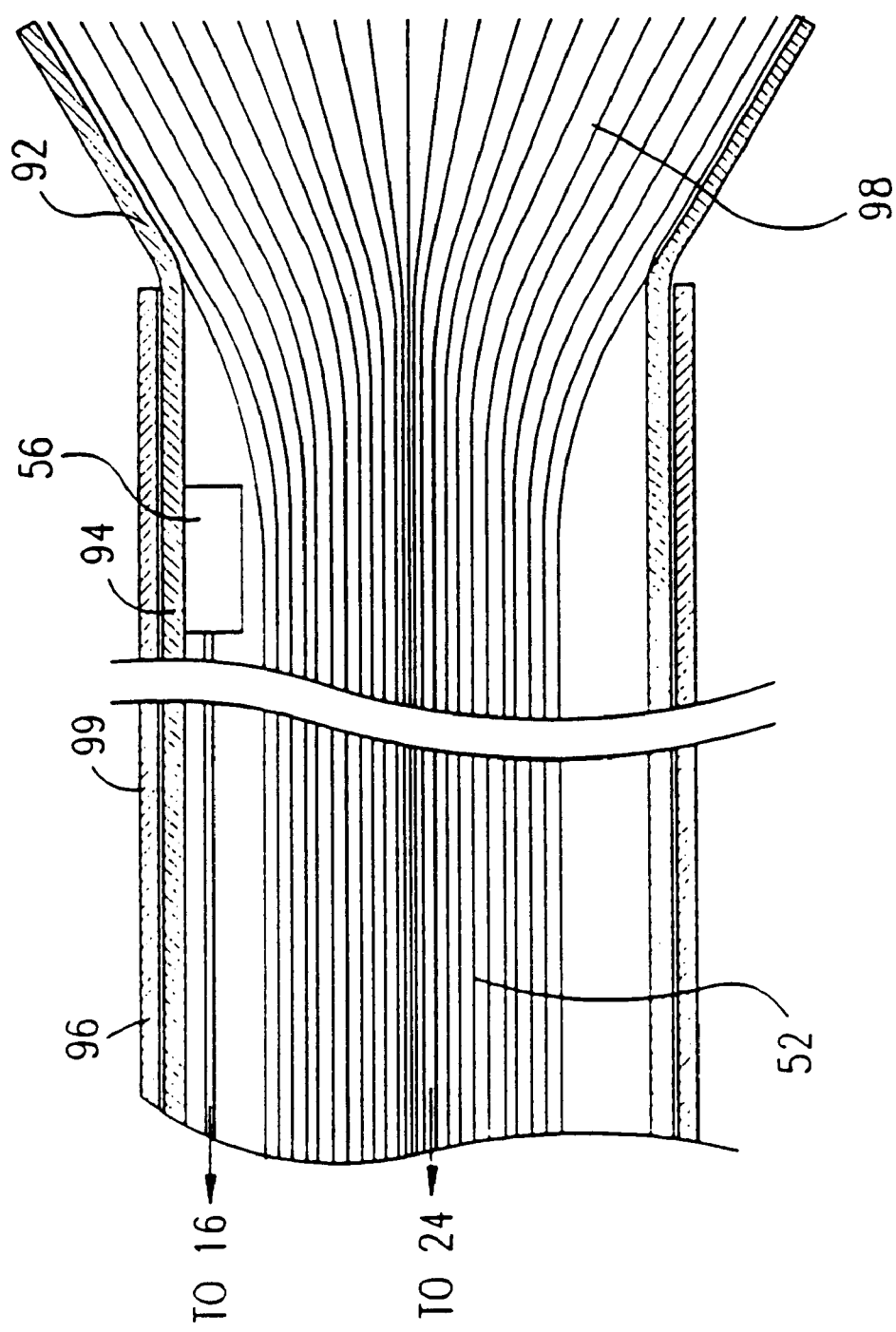

Reference is now made to FIGS. 7A and 7B, which are schematic illustrations showing a catheter 99 having a widening optical tip 92, in accordance with a preferred embodiment of the present invention. Tip 92 is contained in a narrow form, shown in FIG. 7A, during insertion into the heart, and stretches so as to considerably increase the tip area within the heart, as shown in FIG. 7B. Tip 92 comprises an expandable fiberoptic bundle 98, coupled to waveguide 52 and contained within a movable, resilient internal sleeve 94. After catheter 99 is inserted into the heart, sleeve 94 is pushed forward out of an external sleeve 96, allowing bundle 98 to open out to its expanded form, shown in FIG. 7B, so as to irradiate an extended area of the heart wall. Prior to extraction of the catheter from the heart, the operation is reversed, and sleeve 94 is slid back into sleeve 96 so that tip 92 regains its initial compressed dimensions.

Figure 8A:
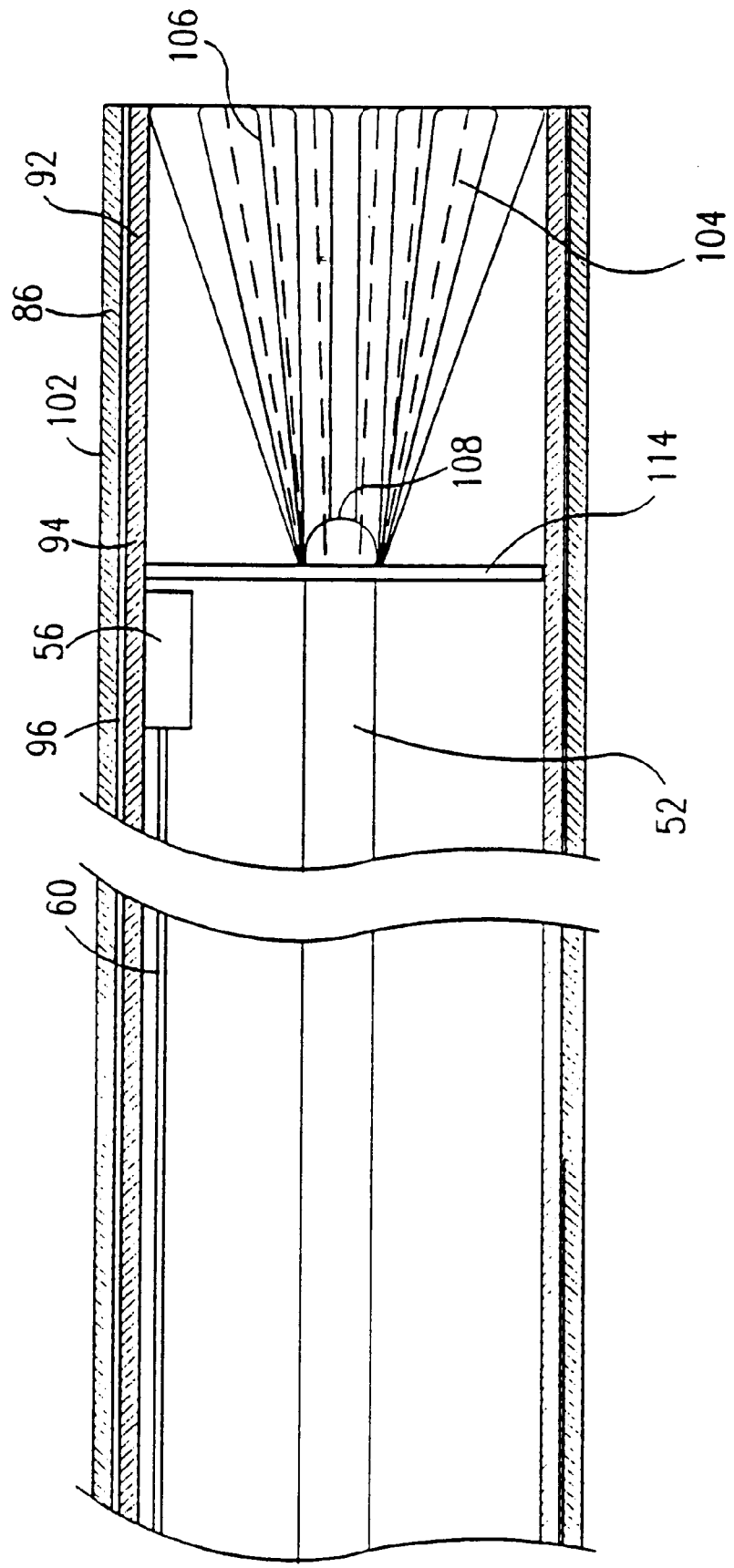

FIGS. 8A, 8B and 8C are schematic illustrations of a catheter 102, having another type of widening optical tip 92, in accordance with an alternative preferred embodiment of the present invention. Catheter 102 is shown in its compressed form in FIG. 8A and in its expanded form in FIG. 8B. FIG. 8C is a schematic, sectional illustration of tip 92 in the configuration of FIG. 8B, taken along line VIIIC—VIIIC.

Tip 92 of catheter 102 comprises a foldable reflector 106, including a plurality of reflective members 104 surrounding a radiation point source 108, which is preferably formed at the distal tip of waveguide 52. Reflector 106 is preferably supported by a suitable mechanical support 114. After insertion of the catheter into the chamber of the heart while in compressed form, internal sleeve 94, along with tip 92 and position sensor 56, is pushed out of outer sleeve 96, so that reflector 106 opens to its expanded form, shown in FIG. 8B. Tip 92 is returned to its initial, compressed form prior to extraction from the body, as described above with respect to FIGS. 7A and 7B.

Figure 9A:
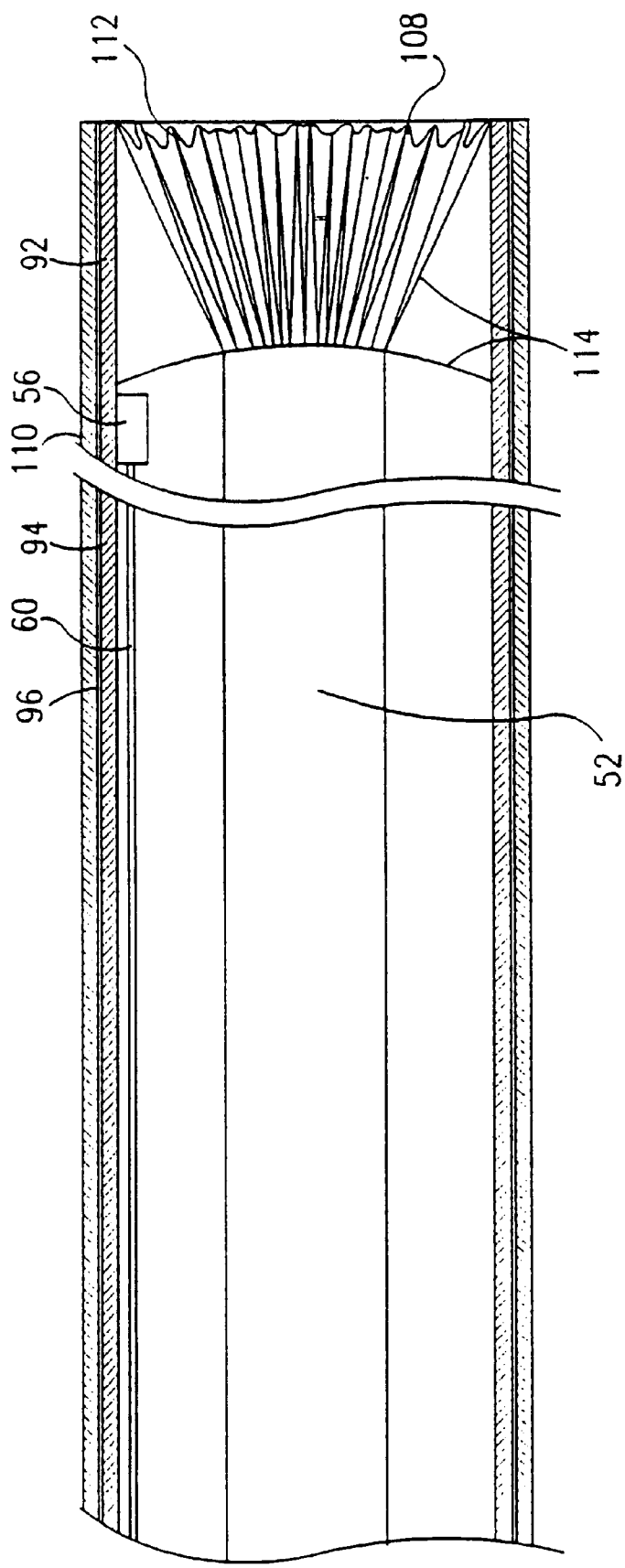
FIGS. 9A and 9B are schematic illustrations of a catheter having a widening optical tip, in closed and open configurations, respectively, in accordance with another preferred embodiment of the present invention.
Figure 9B:
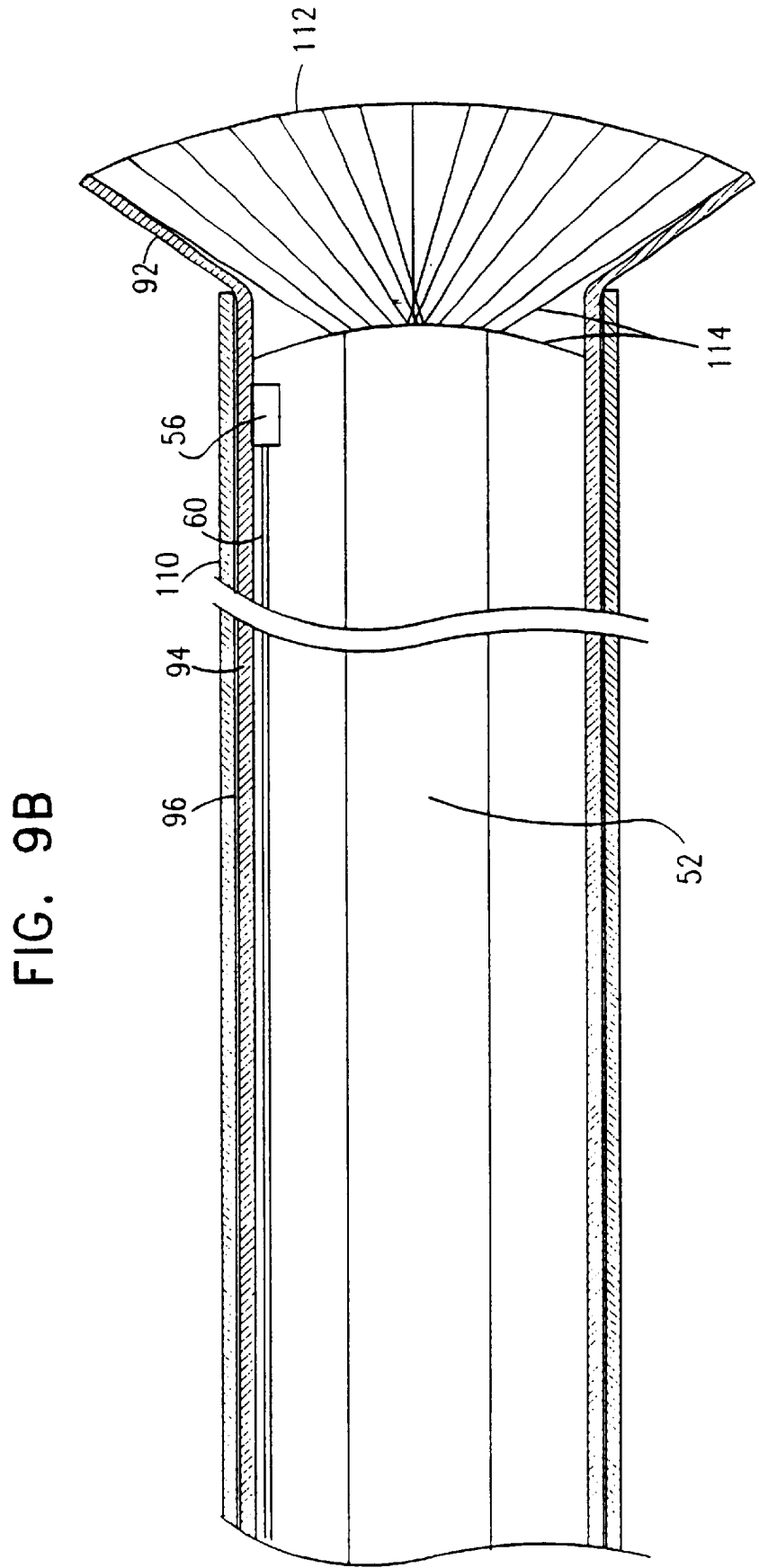

FIGS. 9A and 9B are schematic illustrations of a catheter 110 having a widening optical tip 92, in accordance with still another preferred embodiment of the present invention. Catheter 110 is mechanically switched between its open configuration, shown in FIG. 9A. and its closed configuration, shown in FIG. 9B, by manipulating inner sleeve 94, substantially as described above with respect to FIGS. 7A and 7B. Tip 92 of catheter 110 comprises a radiation scattering optical membrane 112, comprising flexible, translucent plastic material, for example. Membrane 112 is preferably supported on a suitable expansion mechanism 114. The optical membrane, in its expanded form, is brought into contact with the internal heart wall and conveys the radiation emitted from the distal tip of waveguide 52 to the heart tissue over substantially the entire area of the membrane. Scattering within the optical membrane causes the radiation beam emitted from the waveguide to spread over a wide area of the heart wall.

Catheters known in the art for conveying therapeutic radiation to tissues inside the body, such as catheters for LMR, are generally designed to concentrate the radiation on a target at the catheter's distal end. The catheters shown above in FIGS. 3 through 9, and described with reference thereto, differ from such radiation-conveying catheters, in that they are intended to spread the radiation over an extended target area, preferably an area larger than a cross-section of the catheter itself, while still enabling efficient energy transfer from the catheter to the tissue. While the preferred embodiments described herein illustrate certain optical and mechanical designs useful in achieving such objects, those skilled in the art will appreciate that other designs may similarly be used for this purpose, in accordance with the principles of the present invention.

Figure 10:
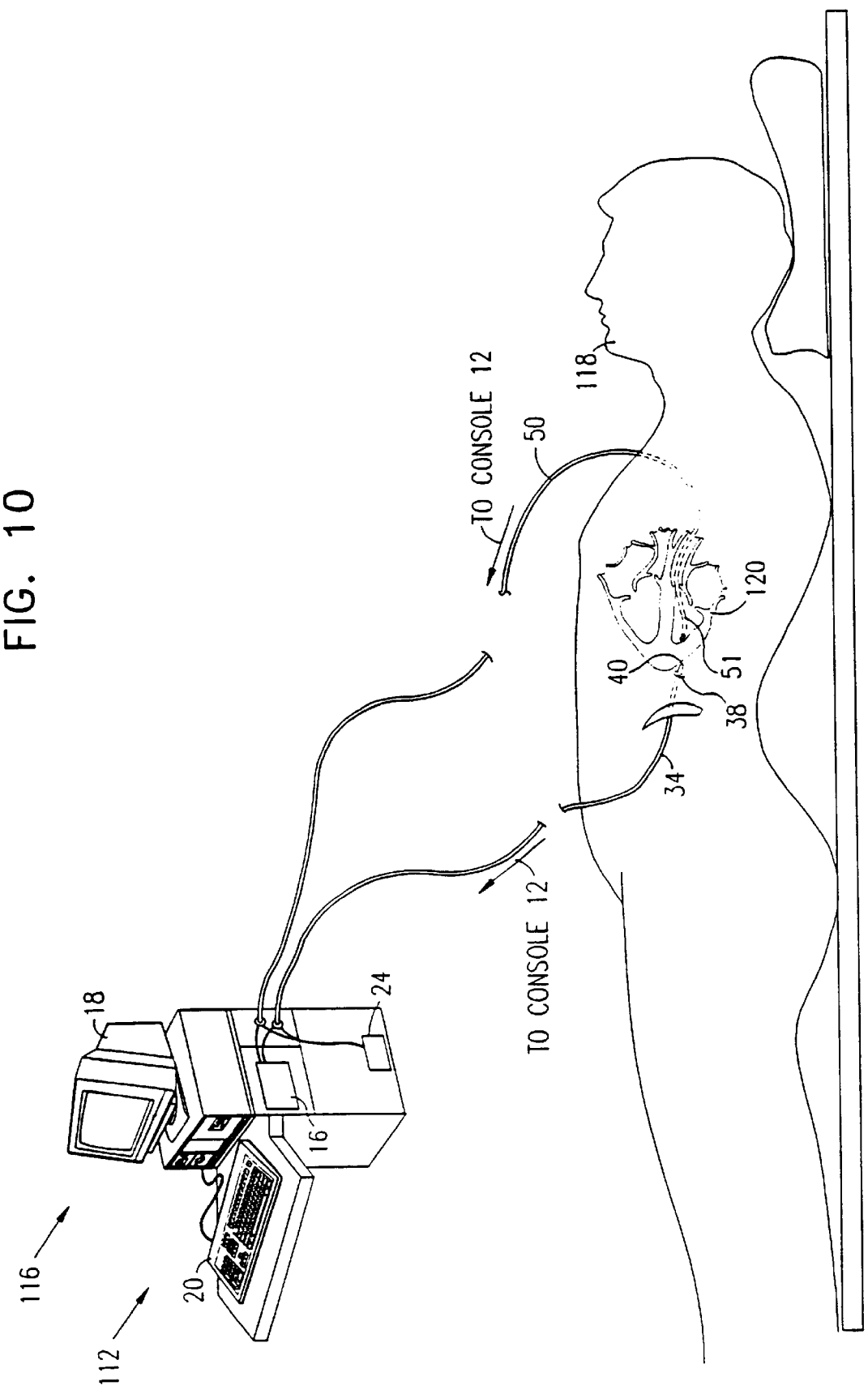
FIG. 10 is a simplified pictorial illustration showing a catheter and a waveguide inserted into a chamber of the heart and chest, respectively, in accordance with an alternative embodiment of the present invention.

FIG. 10 is a schematic illustration showing apparatus 116 for combined invasive and partially invasive biostimulatory irradiation of a section of the heart, in accordance with an alternative preferred embodiment of the present invention. Apparatus 116 comprises a console 112, similar to console 12, as described above with reference to apparatus 48 (FIG. 3A), with both catheter 50 and waveguide 34 (shown in FIG. 2B) coupled thereto. Distal end 36 of waveguide 34 is inserted into the body of a patient 118, as described with reference to FIG. 2B above, and irradiates the patient's heart 120 epicardially. Distal end 51 of catheter 50 is simultaneously inserted into a chamber of heart 120 to irradiate the endocardium. Thus, the ECB irradiation covers an extended area of the ischemic heart tissue from both inside and outside the heart, so that therapeutic levels of radiation reach a relatively greater portion of the thickness of the heart wall than in the other preferred embodiments described above.

It will be appreciated that the preferred embodiments described above are cited by way of example, and the full scope of the invention is limited only by the claims.

What is claimed is:

1. A method of treating a heart comprising the steps of:

identifying an ischemic area of the heart;

providing a plurality of cells;

irradiating the cells in vitro with electromagnetic radiation; and implanting the irradiated cells into the ischemic area of the heart.

2. The method according to claim 1, wherein the electromagnetic radiation provides biostimulation of the cells.

3. The method according to claim 2, wherein the cells are cardiomyocytes.

4. The method according to claim 3, wherein the cardiomyocytes are from embryonic heart muscle.

5. The method according to claim 2, wherein the cells are skeletal muscle cells.

6. The method according to claim 2, wherein the electromagnetic radiation is in the infrared (IR) range.

7. The method according to claim 2, wherein the electromagnetic radiation is in the visible light range.

8. The method according to claim 2, wherein the electromagnetic radiation is in the ultraviolet (UV) range.

\* \* \* \* \*